(12) United States Patent
Dean et al.

(10) Patent No.: US 9,133,178 B2
(45) Date of Patent: Sep. 15, 2015

(54) ALPHA-7 NICOTINIC RECEPTOR MODULATORS FOR THE TREATMENT OF PAIN, A PSYCHOTIC DISORDER, COGNITIVE IMPAIRMENT OR ALZHEIMER'S DISEASE

(75) Inventors: David Dean, Middlesex (GB); Andrew Lightfoot, Middlesex (GB); Susan Roomans, Middlesex (GB)

(73) Assignee: Proximagen Limited, London (GB)

( * ) Notice: Subject to any disclaimer, the term of this patent is extended or adjusted under 35 U.S.C. 154(b) by 255 days.

(21) Appl. No.: 13/881,962

(22) PCT Filed: Oct. 26, 2011

(86) PCT No.: PCT/EP2011/068807
§ 371 (c)(1),
(2), (4) Date: Jul. 1, 2013

(87) PCT Pub. No.: WO2012/055942
PCT Pub. Date: May 3, 2012

(65) Prior Publication Data
US 2013/0310380 A1    Nov. 21, 2013

Related U.S. Application Data

(60) Provisional application No. 61/407,207, filed on Oct. 27, 2010.

(30) Foreign Application Priority Data

Apr. 21, 2011 (GB) .................................. 1106829.3

(51) Int. Cl.
| | | |
|---|---|---|
| C07D 413/14 | (2006.01) |
| C07D 413/10 | (2006.01) |
| A61K 31/506 | (2006.01) |
| A61K 31/5377 | (2006.01) |
| A61K 31/55 | (2006.01) |
| A61K 45/06 | (2006.01) |
| C07D 405/14 | (2006.01) |

(52) U.S. Cl.
CPC ............ *C07D 413/14* (2013.01); *A61K 31/506* (2013.01); *A61K 31/5377* (2013.01); *A61K 31/55* (2013.01); *A61K 45/06* (2013.01); *C07D 405/14* (2013.01); *C07D 413/10* (2013.01)

(58) Field of Classification Search
CPC . C07D 413/14; C07D 413/10; A61K 31/5377
See application file for complete search history.

(56) References Cited

U.S. PATENT DOCUMENTS

| 3,948,894 A | 4/1976 | Lacefield |
| 7,399,765 B2 | 7/2008 | Bunnelle et al. |
| 2005/0101602 A1 | 5/2005 | Basha et al. |

FOREIGN PATENT DOCUMENTS

| EP | 0088593 | 9/1983 |
| EP | 1300399 | 9/2003 |
| EP | 1283056 | 12/2003 |
| WO | 9202513 | 2/1992 |
| WO | 9824782 | 6/1998 |
| WO | 0142241 | 6/2001 |
| WO | 0180893 | 11/2001 |
| WO | 0220500 | 3/2002 |
| WO | 2004029204 | 4/2004 |
| WO | 2005016286 | 2/2005 |
| WO | 2006113704 | 10/2006 |
| WO | 2011064288 | 6/2011 |

OTHER PUBLICATIONS

International Search Report for PCT/EP2011/068807 dated Dec. 9, 2011.

*Primary Examiner* — Rebecca Anderson
(74) *Attorney, Agent, or Firm* — Sean B. Mahoney

(57) ABSTRACT

Compounds are disclosed which modulate the α7 nicotinic acetyl choline receptor (nAChR), having the formula (I) wherein the variables are as specified in the description and claims.

11 Claims, No Drawings

US 9,133,178 B2

ALPHA-7 NICOTINIC RECEPTOR MODULATORS FOR THE TREATMENT OF PAIN, A PSYCHOTIC DISORDER, COGNITIVE IMPAIRMENT OR ALZHEIMER'S DISEASE

CROSS REFERENCE TO RELATED APPLICATION

The present application is the U.S. national stage of International Application PCT/EP2011/068807, filed Oct. 26, 2011, which international application was published on May 3, 2012, as International Publication No. WO2012/055942. The International Application claims priority to U.S. Provisional Application No. 61/407,207, filed Oct. 27, 2010, and British Patent Application No. 11068293, filed Apr. 21, 2011, the contents of which are incorporated herein by reference in their entireties.

FIELD OF THE INVENTION

This invention relates to heterocyclic compounds having activity in modulation of the α7 nicotinic acetylcholine receptor (nAChR). The invention also relates to the use of heterocyclic compounds in treating diseases and conditions mediated by modulation of the α7 nAChR. In addition, the invention relates to compositions containing the heterocyclic compounds and processes for their preparation.

BACKGROUND OF THE INVENTION

The neurotransmitter acetylcholine (ACh), by binding to cholinergic receptors, causes the opening of ion channels within the mammalian system. The central nervous system (CNS) contains two types of ACh receptor, muscarinic receptors and nAChRs. nAChRs are ligand-gated ion channels containing five subunits (for reviews, see Colquhon et al. (1997) Advances in Pharmacology 39, 191-220; Williams et al. (1994) Drug News & Perspectives 7, 205-223; Doherty et al. (1995) Annual reports in Medicinal Chemistry 30, 41-50). The nAChR gene family can be divided into two groups: those coding for β subunits and those coding for α subunits (for reviews, see Karlin & Akabas (1995) Neuron 15, 1231-1244; Sargent (1993) Annu. Rev. Neurosci. 16, 403-443). Three of the α subunits, α7, α8 and α9, can form functional receptors when expressed alone and form homooligomeric receptors.

Studies have indicated that neuronal nicotinic receptors play important roles in modulating neurotransmission, cognition, sensory gating, and anxiety (Zarei et al. Neuroscience 1999, 88, 755-764, Frazier et al. J. Neurosci. 1998, 18, 8228-8235, Radcliffe et al. J. Neurosci. 1998, 18, 7075-7083, Minana et al. Neuropharmacology 1998, 37, 847-857, Albuquerque et al. Toxicol. Lett. 1998, 102-103, 211-218, Neubauer, et al. Neurology 1998, 51, 1608-1612, Stevens et al. Psychopharmacology 1998, 136, 320-327, Adler et al. Schizophrenia Bull. 1998, 24, 189-202.); thus, there has been interest in the use of compounds that modulate these receptors for treating CNS disorders.

A role for α7 receptors in the etiology of schizophrenia has been suggested by linkage studies (Freedman et al, Psychopharmacology (2004), 174(1), 54-64) demonstrating an association between the α7 locus and a sensory gating deficit which represents a major schizophrenia endophenotype. Such gating deficits in patients have been transiently reversed by nicotine with a pharmacology consistent with action via α7. In addition, in animal models, lesion of forebrain cholinergic afferents or pharmacological blockade of α7 receptors elicits similar sensory gating deficits which are also apparent in in-bred mouse strains expressing reduced levels of the α7 receptor. Nicotine has been reported to normalise the deficits in both lesioned animals and in-bred mouse strains, again with a pharmacology compatible with activity at the α7 receptor. Pharmacological blockade of α7 receptors has been reported to impair rodent short-term working memory, whilst receptor activation has been reported to enhance performance in the same paradigm, thus implicating α7 receptors as a target for cognitive enhancement.

α7 nAChRs are characterised by their fast activation kinetics and high permeability to $Ca^{2+}$ compared to other subtypes (Delbono et al. J. Pharmacol. Exp. Ther. 1997, 280, 428-438.) and exhibit rapid desensitization following exposure to agonists. (Castro et al., Neurosci. Lett. 1993, 164, 137-140, Couturier et al., Neuron 1990, 5, 847-856, Alkondon et al., J. Pharmacol. Exp. Ther. 1994, 271, 494-506). Treatment with α7 agonists may therefore be problematic because both acetylcholine and nicotine both show activation followed by blockade and/or desensitisation of the receptor and hence chronic treatment with an agonist may well result in apparent antagonism. In addition, agonists have been shown to exhibit highest affinity for the desensitised state of the receptor and can, thus, mediate receptor desensitisation at concentrations below the threshold for receptor activation (Briggs and McKenna. Neuropharmacology 1998 37, 1095-1102).

This problem may be overcome by treatment with a positive allosteric modulator (PAM). PAMs enhance α7 nAChR activation mediated by endogenous or exogenous agonists without activating the receptor in their own right, i.e. in the absence of agonist. A number of PAMs have been reported (Lightfoot et al. Progress in medicinal chemistry 46:131-71, 2008).

SUMMARY OF THE INVENTION

This invention relates to heterocylic compounds having activity in modulation of the α7 nicotinic acetylcholine receptor (nAChR). The invention also relates to the use of the heterocylic compounds in treating diseases and conditions mediated by modulation of the α7 nAChR. In addition, the invention relates to compositions containing the heterocylic compounds and processes for their preparation.

International Patent Application WO 2006/113704 discloses the general formula of a wide class of compounds encompassing some which have some structural similarities to some of the compounds with which this invention is concerned, but the alleged activity of compounds within that disclosed general formula is modulation of the activity of the CB1 receptor.

International Patent Application WO 9824782 also discloses the general formula of a wide class of compounds encompassing some which have some structural similarities to some of the compounds with which this invention is concerned, but the alleged activity of compounds within that disclosed general formula is inhibition of the activity of TNF alpha, IL-1 beta, IL-6, and/or IL-8.

International Patent Application WO 01/42241 also discloses the general formula of a wide class of compounds encompassing some which have some structural similarities to some of the compounds with which this invention is concerned, but the alleged activity of compounds within that disclosed general formula is inhibition of the cytokine activity.

DETAILED DESCRIPTION OF THE INVENTION

In general, this invention relates to heterocylic compounds having activity in modulation of the α7 nicotinic acetylcholine receptor (nAChR). It is believed that compounds with which the invention is concerned are primarily active at that receptor and lack significant other biological activities. The invention also relates to the use of the heterocylic compounds in treating diseases and conditions mediated by modulation of the α7 nAChR. In addition, the invention relates to compositions containing the compounds and processes for their preparation.

According to a first aspect, the invention provides a compound of formula (I) or a salt thereof:

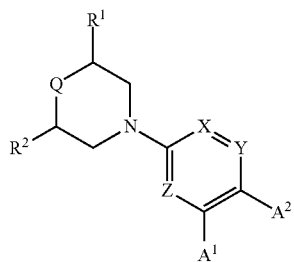

(I)

for use in treating diseases and conditions mediated by modulation of the α7 nicotinic acetyl choline receptor (nAChR), wherein:
X, Y and Z are each independently selected from CH and N;
$A^1$ is isobutyl or a 5 or 6-membered aryl or heteroaryl selected from a carbon-linked phenyl, pyridinyl, pyrimidinyl, furyl, pyrrolyl, thienyl or isoxazolyl, each optionally substituted with one or two substituents independently selected from halo, cyano, methyl, trifluoromethyl, methoxy and trifluoromethoxy, and $A^2$ is a 5 or 6-membered heteroaryl selected from a carbon-linked pyridinyl, pyrimidinyl, furyl, pyrrolyl, thienyl or isoxazolyl, each optionally substituted with one or two substituents independently selected from halo, cyano, methyl, trifluoromethyl, methoxy and trifluoromethoxy;
Q is selected from a bond, —$CH_2$—, —$CH_2CH_2$—, —O—, —S— and N($R^a$)—, wherein $R^a$ is

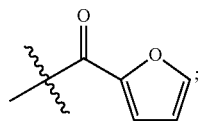 [SMILES: *C(=O)c1ccco1]

$R^1$ and $R^2$ are each individually selected from hydrogen and methyl, with the proviso that when Q is —O—, then $R^1$ and $R^2$ are both methyl.

According to a second aspect, the invention provides a compound of the formula (Ia) or a pharmaceutically acceptable salt thereof:

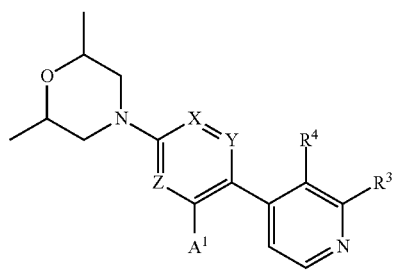

(Ia)

wherein:
X, Y and Z are each independently selected from CH and N;
$A^1$ is selected from a isobutyl and a 5 or 6-membered aryl or heteroaryl, wherein said 5 or 6-membered aryl or heteroaryl is selected from a carbon-linked phenyl, pyridinyl, pyrimidinyl, furyl, pyrrolyl, thienyl or isoxazolyl, each optionally substituted with one or two substituents independently selected from halo, cyano, methyl, trifluoromethyl, methoxy and trifluoromethoxy; and
one of $R^3$ and $R^4$ is hydrogen and the other is methyl.

As used herein, a halo substituent refers to fluoro, chloro, bromo and iodo radicals. In one particular embodiment, unless otherwise indicated, any halo substituent is chloro or bromo.

In an embodiment Y is CH.

As used herein, the term "alkyl" (when used as a group or as part of a group) refers to a straight or branched hydrocarbon radical derived from removal of one hydrogen atom from an alkane containing the specified number of carbon atoms. For example, $C_{1-6}$alkyl means a straight or branched hydrocarbon radical containing at least 1 and at most 6 carbon atoms. Alkyl can for example be, but is not limited to: methyl (Me), ethyl (Et), n-propyl (propyl), isopropyl (1-methylethyl), n-butyl (butyl), isobutyl, sec-butyl, t-butyl, n-pentyl, 3-methylbutyl, 1-ethylpropyl, n-hexyl or isohexyl.

As used herein, "aryl" refers to an aromatic group with at least one ring having a conjugated pi-electron system. In one aspect, "aryl" may be phenyl. If specified herein, the aryl group may be substituted by one or more substituents.

As used herein, "heteroaryl" refers to a cyclic or bicyclic group with at least one ring having a conjugated pi-electron system and comprising at least one, for example one or two, heteroatoms selected from N, O and S. In one aspect the "heteroaryl" group is a 5-, or 6-membered cyclic group. In one aspect, "heteroaryl" moieties are selected from pyridinyl (pyridine group), pyrimidinyl (pyrimidine group), furyl (furan group), pyrrolyl (pyrrole group), thienyl (thiophene group) or isoxazolyl (isoxazole group). Each carbon linked heteroaryl group may be attached at any ring carbon. If specified herein, the heteroaryl group may be substituted by one or more substituents.

The embodiments described below are embodiments of either the first or the second aspect of the invention (as appropriate) unless specified otherwise.

In one embodiment of the first aspect of the invention, the invention provides a compound or a salt thereof for use in treating diseases and conditions mediated by modulation of the α7 nicotinic acetyl choline receptor (nAChR), wherein the compound is a compound of formula (I) as defined above other than:

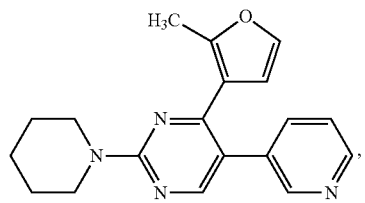

-continued

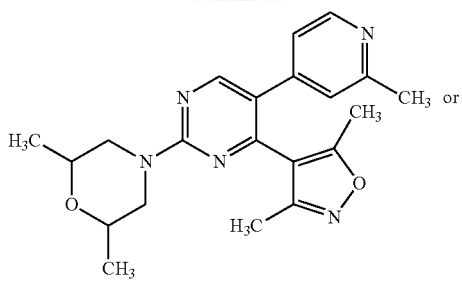

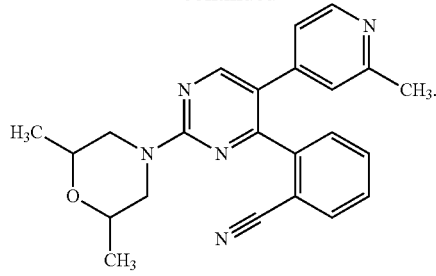

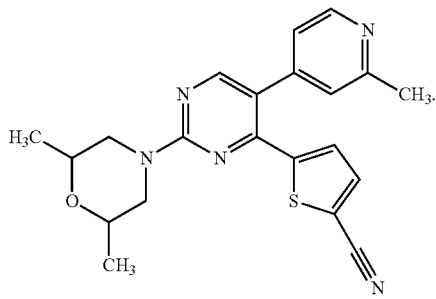

In a further embodiment of the first aspect of the invention, the invention provides a compound or a salt thereof for use in treating diseases and conditions mediated by modulation of the α7 nicotinic acetyl choline receptor (nAChR), wherein the compound is a compound of formula (I) as defined above other than:

In one embodiment of the second aspect of the invention, the invention provides a compound or a salt thereof wherein the compound is a compound of formula (Ia) as defined above other than:

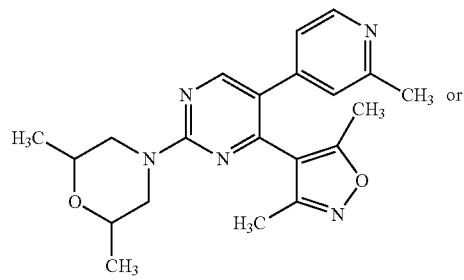

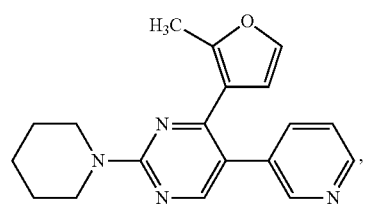

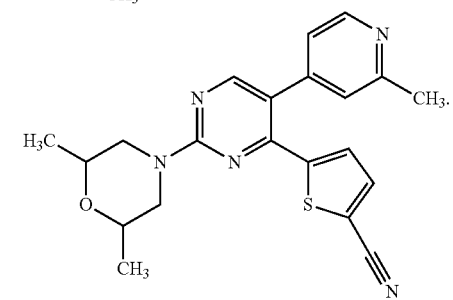

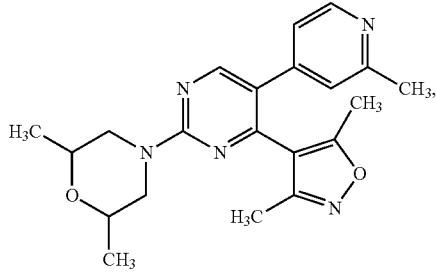

In a further embodiment of the second aspect of the invention, the invention provides a compound or a salt thereof wherein the compound is a compound of formula (Ia) as defined above other than:

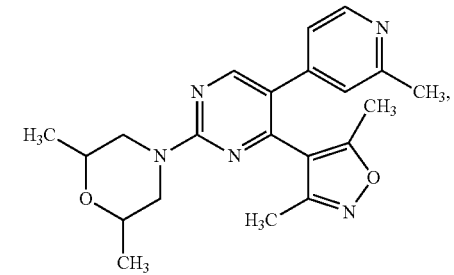

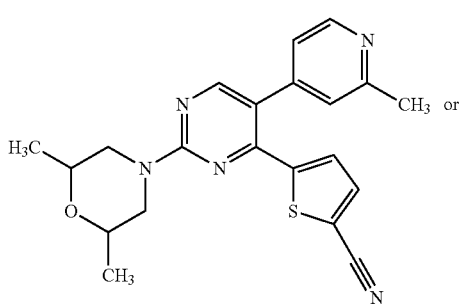

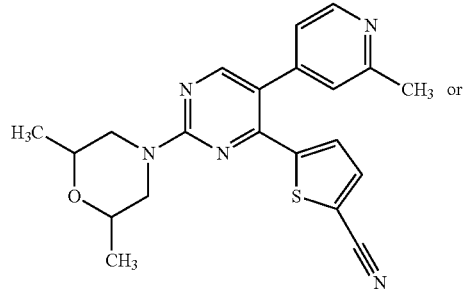

-continued

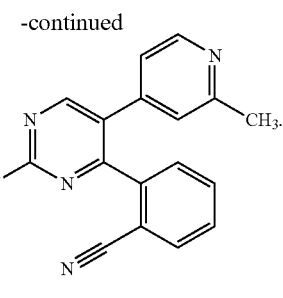

In one embodiment of the first aspect of the invention, Q is selected from a bond, —CH$_2$—, —CH$_2$CH$_2$—, —O—, —S—. In a further embodiment, when Q is CH$_2$CH$_2$—, then R$^1$ and R$^2$ are both H. In a further embodiment, when Q is —S—, then R$^1$ and R$^2$ are both H. In a further embodiment, when Q is —CH$_2$—, then R$^1$ is selected from H and methyl and R$^2$ is H. In a further embodiment, when Q is bond, then R$^1$ and R$^2$ are both H. In a further embodiment, when Q is —CH$_2$CH$_2$—, then R$^1$ and R$^2$ are both H. In one particular embodiment, either: Q is selected from a bond, —CH$_2$CH$_2$— and —S—, and R$^1$ and R$^2$ are both H; Q is —CH$_2$—, R$^1$ is selected from H and methyl and R$^2$ is H; or Q is —O— and R$^1$ and R$^2$ are both methyl.

In one embodiment of the invention, for example, an embodiment of the second aspect of the invention, Z is CH or N and either X and Y are both CH, or one of X and Y is CH and the other is N.

In one embodiment of the first or second aspects of the invention, A$^1$ is 5 or 6-membered aryl or heteroaryl, selected from a carbon-linked phenyl, pyridinyl, pyrimidinyl, furyl, pyrrolyl, thienyl or isoxazolyl, each optionally substituted with one or two substituents independently selected from halo, cyano, methyl, trifluoromethyl, methoxy and trifluoromethoxy.

In one embodiment of the first or second aspects of the invention, when A$^1$ is 5 or 6-membered aryl or heteroaryl, said 5 or 6-membered aryl or heteroaryl is selected from phenyl, pyridinyl or furyl. In one embodiment, when A$^1$ is 5 or 6-membered aryl or heteroaryl, said aryl or heteroaryl is optionally substituted with one or two groups selected from halo (for example fluoro or chloro), cyano, methyl, trifluoromethyl and methoxy. In a further embodiment, when A$^1$ is 5 or 6-membered aryl or heteroaryl, said aryl or heteroaryl is optionally substituted with one or two groups selected from halo (for example, fluoro), cyano, methyl and trifluoromethyl. In one embodiment, when A$^1$ is 5 or 6-membered heteroaryl, said heteroaryl is optionally substituted with one or two groups selected from fluoro, chloro, methyl and trifluoromethyl. In a further embodiment, when A$^1$ is 5 or 6-membered heteroaryl, said heteroaryl is optionally substituted with one or two groups selected from fluoro, methyl and trifluoromethyl. In a yet further embodiment, when A$^1$ is 5 or 6-membered heteroaryl, said heteroaryl is unsubstituted or substituted with one or two methyl groups. In one embodiment, when A$^1$ is phenyl, said phenyl is optionally substituted with one or two groups selected from halo (for example fluoro or chloro), cyano, methyl, trifluoromethyl and methoxy. In a further embodiment, when A$^1$ is phenyl, said phenyl is optionally substituted with one or two groups selected from halo (for example, fluoro), cyano, methyl and trifluoromethyl.

In one embodiment of the second aspect of the invention, A$^1$ is selected from isobutyl and 5 or 6-membered aryl or heteroaryl, said aryl or or heteroaryl being selected from a carbon-linked phenyl, pyridinyl or furyl each optionally substituted with one or two substituents independently selected from halo, cyano, methyl, trifluoromethyl, methoxy and trifluoromethoxy, especially halo (for example, fluoro), cyano, methyl and trifluoromethyl.

In one embodiment of the first aspect of the invention, A$^2$ is a 5 or 6-membered heteroaryl optionally substituted with one or two substituents selected from methyl, trifluoromethyl, methoxy and trifluoromethoxy, for example, methyl or methoxy, especially methyl. In another embodiment, A$^2$ is a 5 or 6-membered heteroaryl optionally substituted with one methyl group. In one embodiment, A$^2$ is a 5 or 6-membered heteroaryl selected from a carbon-linked pyridinyl, pyrimidinyl, furyl and isoxazolyl, each optionally substituted as described above. In a further embodiment, A$^2$ is a 5 or 6-membered heteroaryl selected from a carbon-linked pyridinyl, pyrimidinyl, furyl and furyl, for example a carbon-linked pyridinyl, each optionally substituted as described above. In one embodiment, A$^2$ is selected from unsubstituted pyridinyl optionally substituted with one methyl, pyrimidinyl substituted with two methoxy groups, furyl optionally substituted with one methyl and isoxazolyl optionally substituted with one methyl. In a further embodiment, A$^2$ is selected from unsubstituted pyridinyl and pyridinyl substituted with one methyl, especially pyridinyl substituted with one methyl. In a yet further embodiment, when A$^2$ is optionally substituted pyridinyl, then A$^2$ is selected from 4-pyridinyl, 2-methyl-4-pyridinyl, 3-methyl-4-pyridinyl, 2-methyl-3-pyridinyl and 2-pyridinyl, especially 4-pyridinyl, 2-methyl-4-pyridinyl or 3-methyl-4-pyridinyl, in particular 2-methyl-4-pyridinyl. In a yet further embodiment, when A$^2$ is optionally substituted pyridinyl, then A$^2$ is other than unsubstituted 3-pyridinyl.

In one embodiment of the second aspect of the invention, R$^3$ is methyl and R$^4$ is hydrogen.

Examples of compounds of the invention, include the compounds of list A:

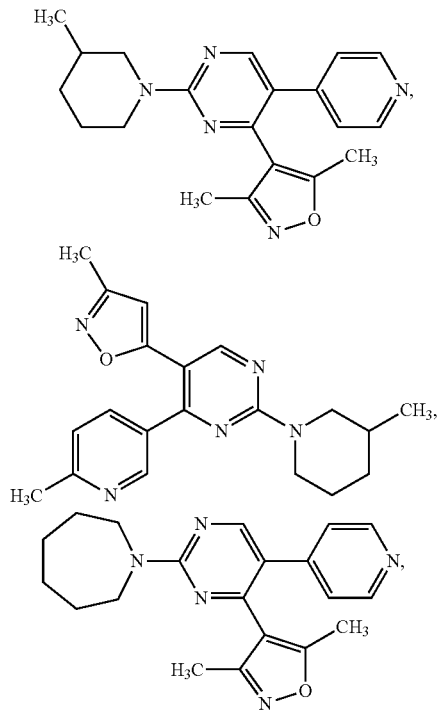

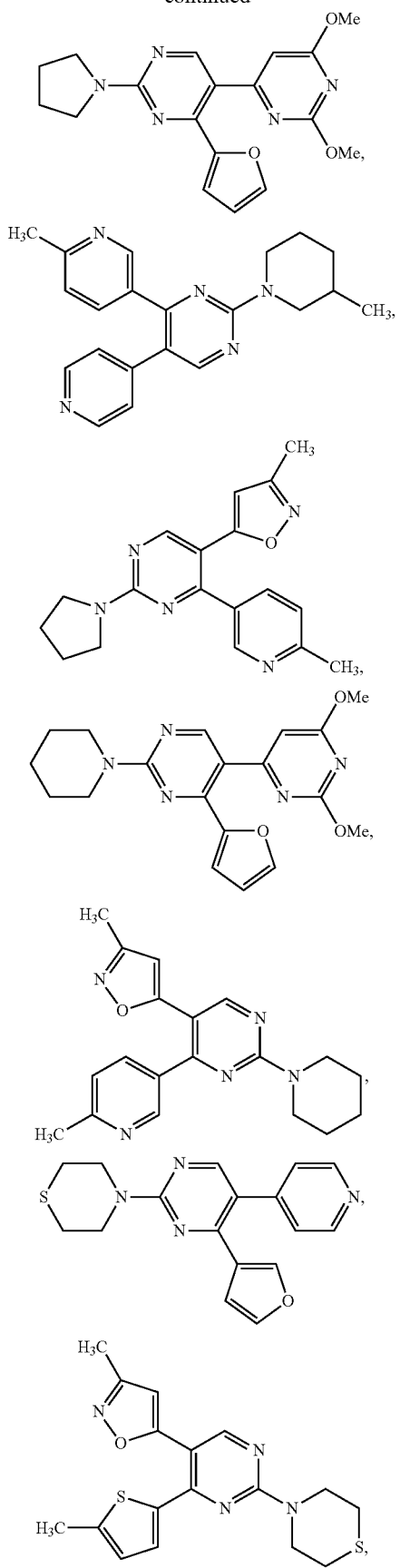
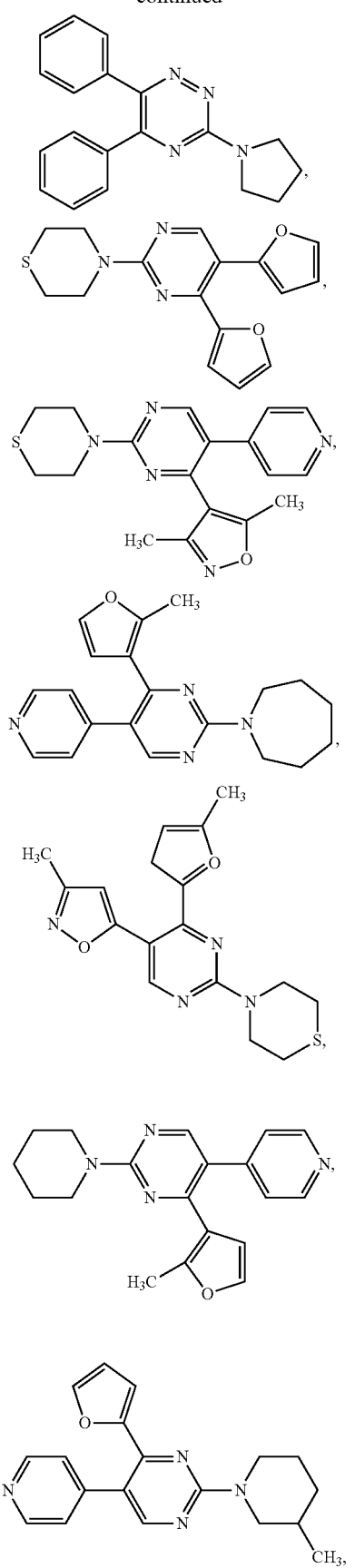

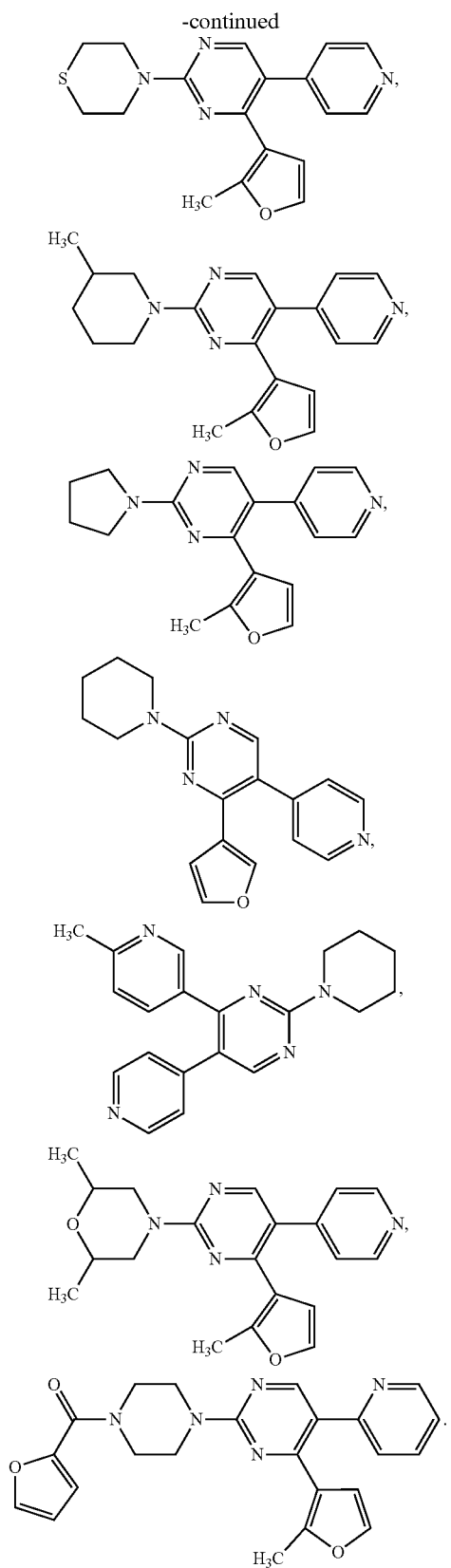

Further examples of compounds of the invention include compounds of list B:

4-(2-Methyl-3-furanyl)-2-(3-methyl-1-piperidinyl)-5-(4-pyridinyl)pyrimidine

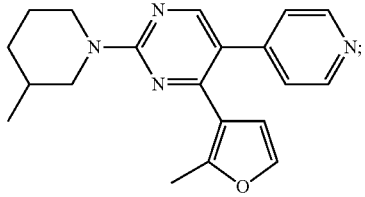

4-(2-Methyl-3-furanyl)-2-(3-methyl-1-piperidinyl)-5-(3-pyridinyl)pyrimidine

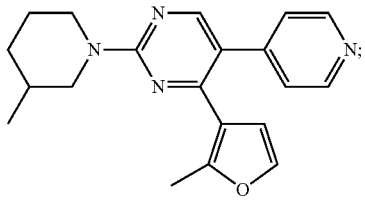

4-(2-Methyl-3-furanyl)-2-(3-methyl-1-piperidinyl)-5-(2-methyl-4-pyridinyl)pyrimidine

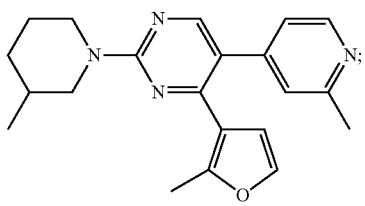 [SMILES: Cc1cc(-c2cnc(N3CCCC(C)C3)nc2-c2ccoc2C)ccn1]

4-(2-Methyl-3-furanyl)-5-(2-methyl-4-pyridinyl)-2-(1-piperidinyl)pyrimidine

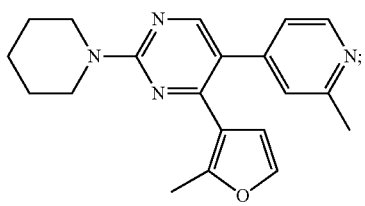 [SMILES: Cc1cc(-c2cnc(N3CCCCC3)nc2-c2ccoc2C)ccn1]

cis-2,6-Dimethyl-4-[4-(2-methyl-3-furanyl)-5-(2-methyl-4-pyridinyl)-2-pyrimidinyl]morpholine

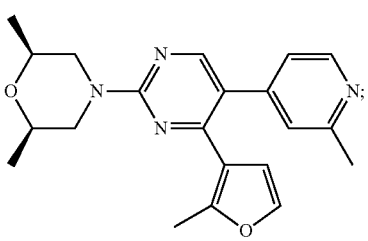 [SMILES: Cc1cc(-c2cnc(N3C[C@@H](C)O[C@@H](C)C3)nc2-c2ccoc2C)ccn1]

In one embodiment of the first aspect of the invention, the compound of formula (I) is a compound of list A or a pharmaceutically acceptable salt thereof.

trans-2,6-Dimethyl-4-[4-(2-methyl-3-furanyl)-5-(2-methyl-4-pyridinyl)-2-pyrimidinyl]morpholine

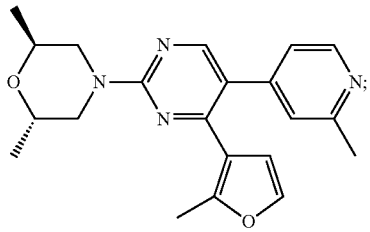 [SMILES: Cc1cc(-c2cnc(N3C[C@H](C)O[C@@H](C)C3)nc2-c2ccoc2C)ccn1]

1-[4-(2-Methyl-3-furanyl)-5-(2-pyridinyl)-2-pyrimidinyl]hexahydro-1H-azepine

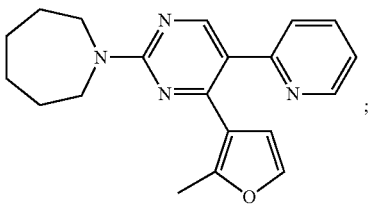 [SMILES: Cc1occc1-c1nc(N2CCCCCC2)ncc1-c1ccccn1]

4-(2-Methyl-3-furanyl)-2-(3-methyl-1-piperidinyl)-5-(2-pyridinyl)pyrimidine

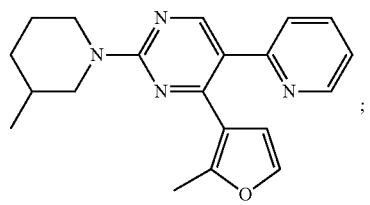 [SMILES: Cc1occc1-c1nc(N2CCCC(C)C2)ncc1-c1ccccn1]

cis-2,6-Dimethyl-4-[4-(2-methylpropyl)-5-(2-methyl-4-pyridinyl)-2-pyrimidinyl]morpholine

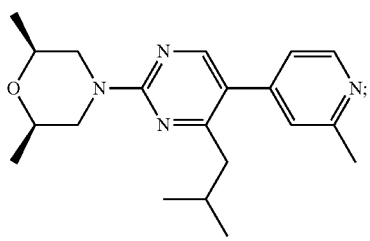 [SMILES: Cc1cc(-c2cnc(N3C[C@@H](C)O[C@@H](C)C3)nc2CC(C)C)ccn1]

cis-2,6-Dimethyl-4-[6-(2-methyl-3-furanyl)-5-(2-methyl-4-pyridinyl)-2-pyrazinyl]morpholine

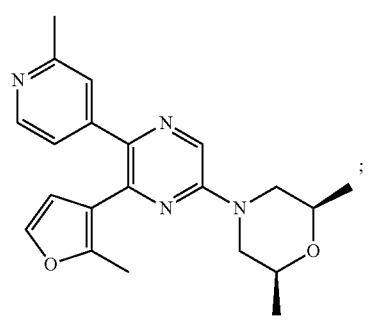 [SMILES: Cc1cc(-c2ncc(N3C[C@@H](C)O[C@@H](C)C3)nc2-c2ccoc2C)ccn1]

6-(cis-2,6-dimethyl-4-morpholinyl)-2'-methyl-4-(2-methyl-3-furanyl)-3,4'-bipyridine

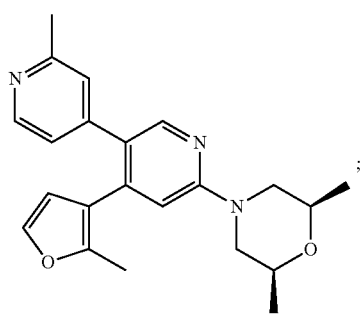 [SMILES: Cc1cc(-c2cnc(N3C[C@@H](C)O[C@@H](C)C3)cc2-c2ccoc2C)ccn1]

6-(cis-2,6-dimethyl-4-morpholinyl)-2'-methyl-2-(2-methyl-3-furanyl)-3,4'-bipyridine

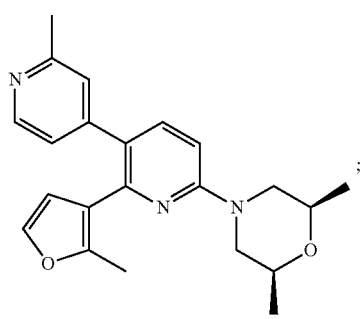 [SMILES: Cc1cc(-c2ccc(N3C[C@@H](C)O[C@@H](C)C3)nc2-c2ccoc2C)ccn1]

cis-2,6-Dimethyl-4-[3-(2-methyl-3-furanyl)-4-(2-methyl-4-pyridinyhphenyl]morpholine

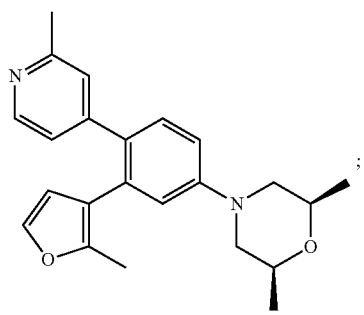 [SMILES: Cc1cc(-c2ccc(N3C[C@@H](C)O[C@@H](C)C3)cc2-c2ccoc2C)ccn1]

cis-2,6-Dimethyl-4-[4-(2-methylphenyl)-5-(2-methyl-4-pyridinyl)-2-pyrimidinyl]morpholine

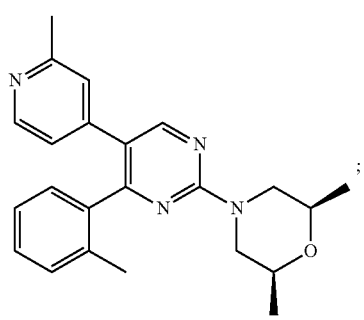 [SMILES: Cc1cc(-c2cnc(N3C[C@@H](C)O[C@@H](C)C3)nc2-c2ccccc2C)ccn1]

cis-2,6-dimethyl-4-[4-(2-methyl-3-furanyl)-5-(3-methyl-4-pyridinyl)-2-pyrimidinyl]morpholine

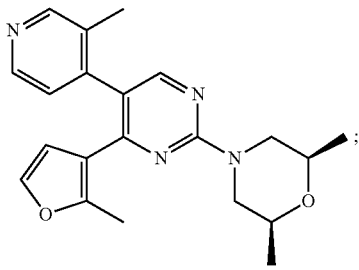 [SMILES: Cc1cnccc1-c1cnc(N2C[C@@H](C)O[C@@H](C)C2)nc1-c1ccoc1C]

cis-2,6-Dimethyl-4-{5-(2-methyl-4-pyridinyl)-4-[2-(trifluoromethyl)-3-pyridinyl]-2-pyrimidinyl}morpholine

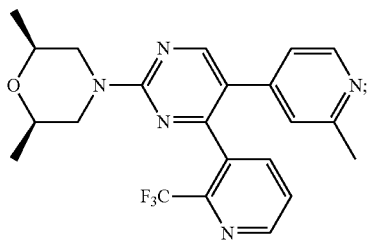 [SMILES: Cc1cc(-c2cnc(N3C[C@@H](C)O[C@@H](C)C3)nc2-c2cccnc2C(F)(F)F)ccn1]

cis-4-[4-(6-Fluoro-4-methyl-3-pyridinyl)-5-(2-methyl-4-pyridinyl)-2-pyrimidinyl]-2,6-dimethylmorpholine

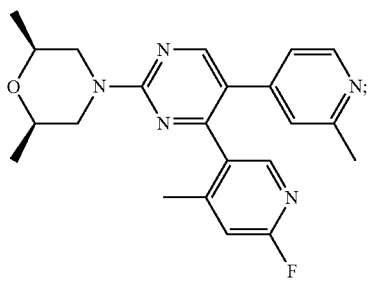 [SMILES: Cc1cc(-c2cnc(N3C[C@@H](C)O[C@@H](C)C3)nc2-c2cnc(F)cc2C)ccn1]

cis-2-[2-(2,6-Dimethyl-4-morpholinyl)-5-(2-methyl-4-pyridinyl)-4-pyrimidinyl]-4-fluorobenzonitrile

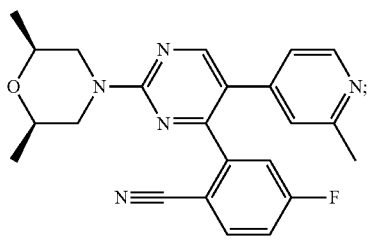 [SMILES: Cc1cc(-c2cnc(N3C[C@@H](C)O[C@@H](C)C3)nc2-c2cc(F)ccc2C#N)ccn1]

and
cis-2-[2-(2,6-dimethyl-4-morpholinyl)-5-(2-methyl-4-pyridinyl)-4-pyrimidinyl]-6-(trifluoromethyl)benzonitrile

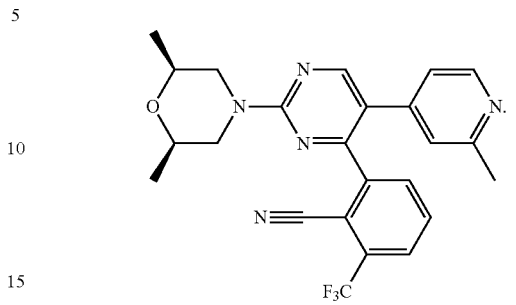

In one embodiment, the invention provides a compound of list B or a salt thereof, for example, the hydrochloride salt thereof. In a further embodiment, the invention provides the compound or salt of any one of Examples 1 to 19 described below. In a yet further embodiment, the invention provides cis-4-[4-(6-fluoro-4-methyl-3-pyridinyl)-5-(2-methyl-4-pyridinyl)-2-pyrimidinyl]-2,6-dimethylmorpholine or a pharmaceutically acceptable salt thereof, for example, the hydrochloride salt thereof.

It will be appreciated that the present invention is intended to include compounds having any combination of the embodiments defined hereinbefore.

For the avoidance of doubt, unless otherwise indicated, the term "substituted" means substituted by one or more defined groups. In the case where groups may be selected from a number of alternative groups, the selected groups may be the same or different.

For the avoidance of doubt, the term "independently" means that where more than one substituent is selected from a number of possible substituents, those substituents may be the same or different.

The compounds of formula (I) may form pharmaceutically acceptable salts, for example, non-toxic acid addition salts formed with inorganic acids such as hydrochloric, hydrobromic, hydroiodic, sulfuric and phosphoric acid, with carboxylic acids or with organo-sulfonic acids. Examples include the HCl, HBr, HI, sulfate or bisulfate, nitrate, phosphate or hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate salts. For reviews on suitable pharmaceutical salts see Berge et al, J. Pharm, Sci., 66, 1-19, 1977; P L Gould, International Journal of Pharmaceutics, 33 (1986), 201-217; and Bighley et al, Encyclopedia of Pharmaceutical Technology, Marcel Dekker Inc, New York 1996, Volume 13, page 453-497.

In one embodiment the salt of the compound of formula (I) is a pharmaceutically acceptable salt, for example an HCl salt.

Hereinafter, the compounds of formula (I) and their pharmaceutically acceptable salts, are referred to as "the compounds of the invention".

It will be appreciated by those skilled in the art that certain protected derivatives of the compounds of the invention, which may be made prior to a final deprotection stage, may not possess pharmacological activity as such, but may, in certain instances, be administered orally or parenterally and thereafter metabolised in the body to form compounds defined in the first aspect which are pharmacologically active. Such derivatives may therefore be described as "prodrugs". All protected derivatives and prodrugs of compounds defined in the first aspect are included within the scope of the invention. Examples of suitable pro-drugs for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within the compound defined in the first aspect.

The compounds of the invention or their salts may exist in solvated or hydrated form.

The compounds of the invention or their salts or solvates/hydrates of the compounds or their salts, may exist in crystalline form, for example, in one or more polymorphic forms.

Therefore, according to a further aspect, the invention provides a solvate, hydrate or prodrug of the compounds of the invention.

Certain compounds of the invention may exist in one or more tautomeric forms. All tautomers and mixtures thereof are included in the scope of the present invention.

Certain compounds of the invention may possess one or more chiral centres and so exist in a number of stereoisomeric forms. Compounds having one chiral centre may exist as enantiomers or a racemic mixture containing enantiomers. Compounds having two or more chiral centres may exist as diastereoisomers or enantiomers. All stereoisomers (for example enantiomers and diastereoisomers) and mixtures thereof are included in the scope of the present invention. Racemic mixtures may be separated to give their individual enantiomer using preparative HPLC using a column with a chiral stationary phase or resolved to yield individual enantiomers utilising methods known to those skilled in the art. In addition, chiral intermediate compounds may be resolved and used to prepare individual enantiomers.

The invention also includes all suitable isotopic variations of the compounds of the invention.

Compounds of the invention may be prepared in a variety of ways. In the following reaction schemes and hereinafter, unless otherwise stated Q, X, Y, Z, $A^1$, $A^2$, $R^1$ and $R^2$ are as defined in the first aspect of the invention. These processes form further aspects of the invention.

Throughout the specification, general formulae are designated by Roman numerals (I), (II), (III), (IV) etc. Subsets of these general formulae are defined as (Ia), (Ib), (Ic), etc. ... (IVa), (IVb), (IVc) etc.

Compounds of formula (Ib) are compounds of the formula (I) wherein X and Z are both N and Y is CH. Compounds of formula (Ib) may be prepared according to scheme 1 by reaction of compounds of formula (II) with compounds of formula (III) as shown in Scheme 1:

Scheme 1

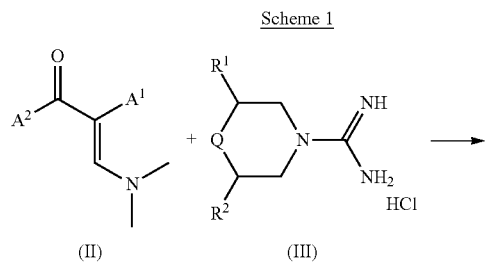

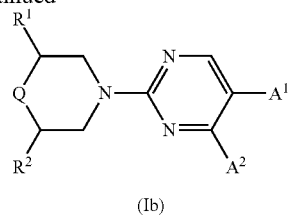

(Ib)

For example, compounds of the formula (Ic), which are compounds of the formula (Ib) wherein $A^1$ is 4-pyridinyl, optionally substituted at the 2-position with methyl (i.e. $R^3$ is selected from hydrogen or methyl), and $A^2$ is 2-methyl-3-furanyl, may be prepared according to scheme 1a by reaction of compounds of formula (IIa), which are compounds of the formula (II) in which $A^1$ is 4-pyridinyl, optionally substituted at the 2-position with methyl, and $A^2$ is 2-methyl-3-furanyl, with compounds of formula (III) as shown in scheme 1A.

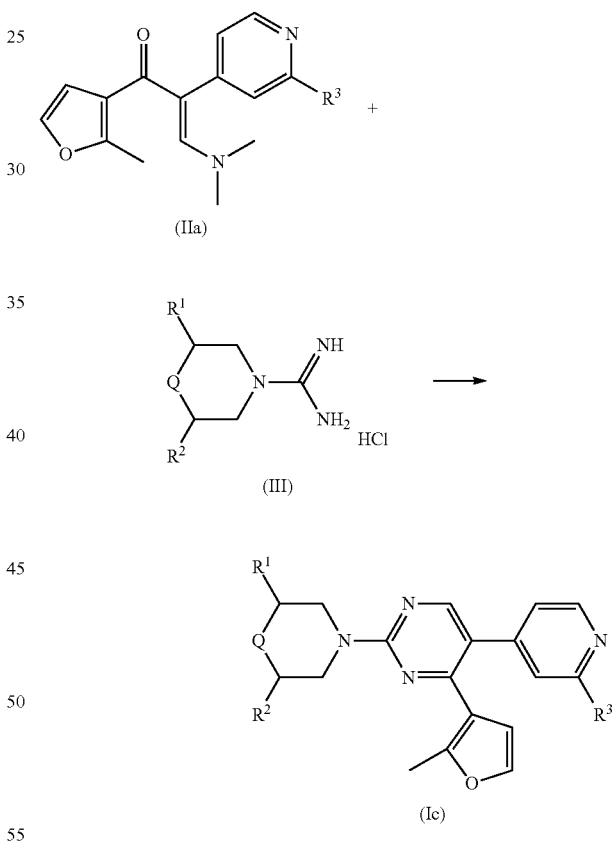

Typical conditions for the reaction of compounds of formula (II) with compounds of formula (III) comprise treatment with a suitable base, such as potassium tert-butoxide, in a suitable solvent, such as ethanol, at reflux.

Compounds of the formula (IIa) may be prepared from the reaction of compounds of the formula (IV) with DMF-DMA (N,N-dimethylformaide dimethylacetal) as shown in scheme 2. Compounds of the formula (IV) may be prepared from the reaction of compounds of the formula (V) with compounds of the formula (VI). Compounds of the formula (V) may be prepared from compounds of the formula (VII):

Scheme 2

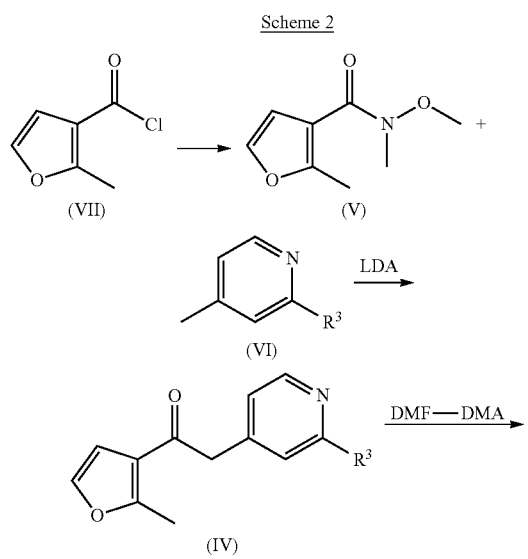

Scheme 4a

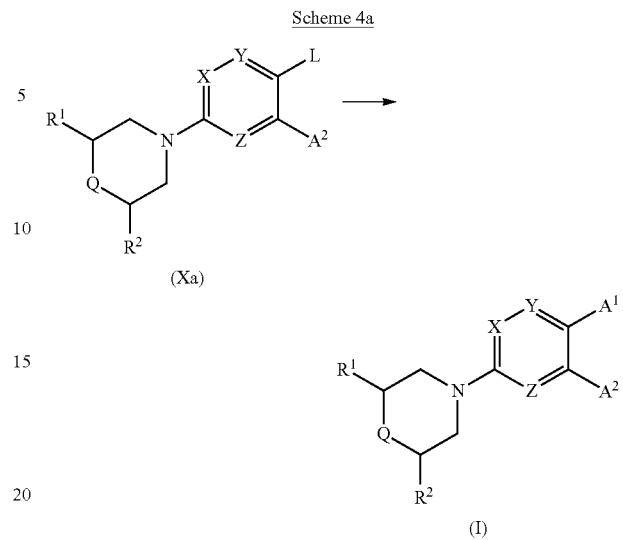

Compounds of the formula (III) may be prepared from the reaction of compounds of the formula (VIII) with compounds of the formula (IX) as shown in scheme 3:

Scheme 3

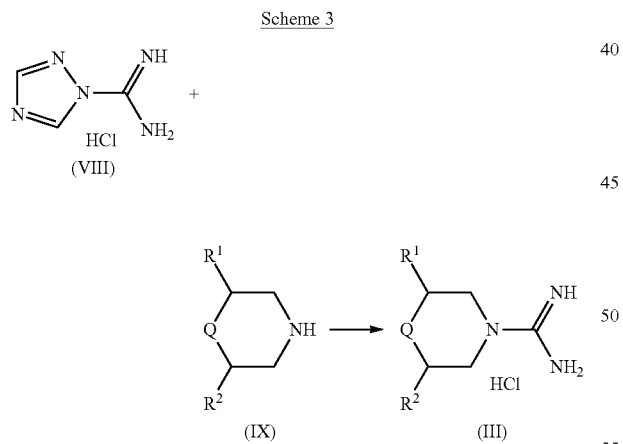

Typical conditions for the reaction of compounds of the formula (VIII) with compounds of the formula (IX) comprise treatment with a base, such as diisopropylethylamine, in a suitable solvent, such as N,N-dimethylformamide, at room temperature.

Alternatively, compounds of formula (I) may be prepared from compounds of formula (VIIIa) or (VIIIb) according to schemes 4a and 4b. Compounds of formula (Xa) or (Xb) include a leaving group L on the central aryl or heteroaryl ring that may be substituted for a group $A^1$ or $A^2$ as appropriate.

Scheme 4b

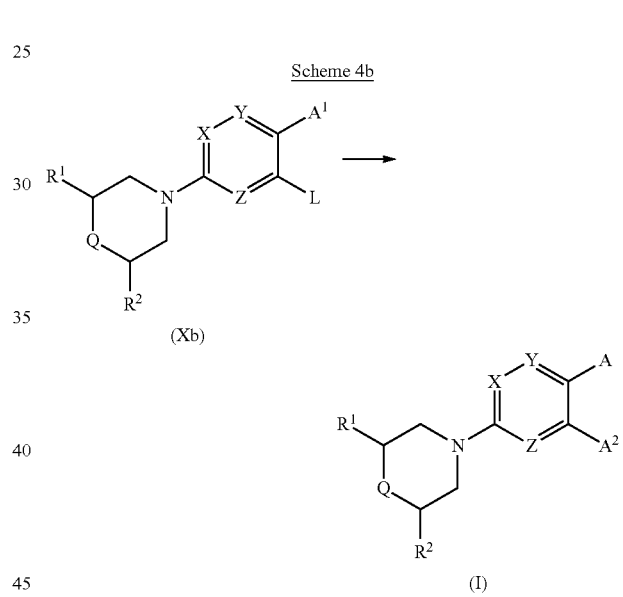

Compounds of the formula (Xa) and (Xb) may be formed from compounds of the formula (XIa) and (XIb) respectively as shown in Scheme 5a and 5b:

Scheme 5a

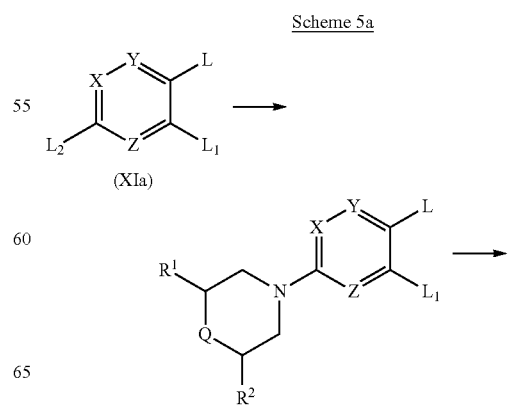

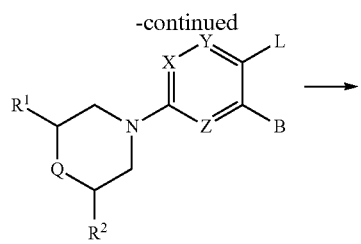

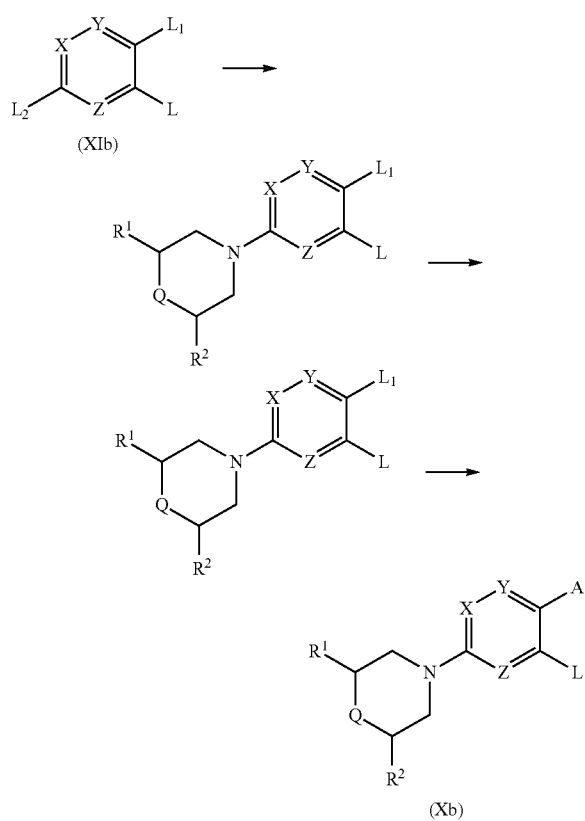

Scheme 5b

Salts may be prepared conventionally by reaction with the appropriate acid or acid derivative, for example, hydrochloric acid.

Uses of Compounds of the Invention

The compounds of the invention may be useful for the treatment of diseases and conditions mediated by positive allosteric modulation of the α7 nAChR or diseases and conditions which are associated with modulation of the α7 nAChR. Diseases or conditions mediated by positive allosteric modulation of the α7 nAChR or diseases and conditions which are associated with modulation of the α7 nAChR include (the numbers in brackets after the listed diseases below refer to the classification code in Diagnostic and Statistical Manual of Mental Disorders, 4th Edition, published by the American Psychiatric Association (DSM-IV) and/or the International Classification of Diseases, 10th Edition (ICD-10):

i) Psychotic disorders for example Schizophrenia (including the subtypes Paranoid Type (295.30), Disorganised Type (295.10), Catatonic Type (295.20), Undifferentiated Type (295.90) and Residual Type (295.60)); Schizophreniform Disorder (295.40); Schizoaffective Disorder (295.70) (including the subtypes Bipolar Type and Depressive Type); Delusional Disorder (297.1) (including the subtypes Erotomanic Type, Grandiose Type, Jealous Type, Persecutory Type, Somatic Type, Mixed Type and Unspecified Type); Brief Psychotic Disorder (298.8); Shared Psychotic Disorder (297.3); Psychotic Disorder due to a General Medical Condition (including the subtypes with Delusions and with Hallucinations); Substance-Induced Psychotic Disorder (including the subtypes with Delusions (293.81) and with Hallucinations (293.82)); and Psychotic Disorder Not Otherwise Specified (298.9).

ii) cognitive impairment including for example the treatment of impairment of cognitive functions including attention, orientation, learning disorders, memory (i.e. memory disorders, amnesia, amnesic disorders, transient global amnesia syndrome and age-associated memory impairment) and language function; as well as cognitive impairment as a result of stroke, Alzheimer's disease, Huntington's disease, Pick disease, Aids-related dementia or other dementia states such as Multiinfarct dementia, alcoholic dementia, hypotiroidism-related dementia, and dementia associated to other degenerative disorders such as cerebellar atrophy and amyotropic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, mild cognitive impairment, age related cognitive impairment, autism related cognitive impairment, Down's syndrome, cognitive deficit related to other diseases such as schizophrenia, bipolar disorder, depression and other psychiatric disorders, and post-electroconvulsive treatment related cognitive disorders; and dyskinetic disorders such as Parkinson's disease, neuroleptic-induced parkinsonism, and tardive dyskinesias.

iii) Depression and mood disorders for example Depressive Episodes (including Major Depressive Episode, Manic Episode, Mixed Episode and Hypomanic Episode); Depressive Disorders (including Major Depressive Disorder, Dysthymic Disorder (300.4), Depressive Disorder Not Otherwise Specified (311)); Bipolar Disorders (including Bipolar I Disorder, Bipolar II Disorder (i.e. Recurrent Major Depressive Episodes with Hypomanic Episodes) (296.89), Cyclothymic Disorder (301.13) and Bipolar Disorder Not Otherwise Specified (296.80)); Other Mood Disorders (including Mood Disorder due to a General Medical Condition (293.83) which includes the subtypes With Depressive Features, With Major Depressive-like Episode, With Manic Features and With Mixed Features); Substance-Induced Mood Disorder (including the subtypes With Depressive Features, With Manic Features and With Mixed Features); and Mood Disorder Not Otherwise Specified (296.90).

iv) Anxiety disorders for example Social Anxiety Disorder; Panic Attack; Agoraphobia, Panic Disorder; Agoraphobia Without History of Panic Disorder (300.22); Specific Phobia (300.29) (including the subtypes Animal Type, Natural Environment Type, Blood-Injection-Injury Type, Situational Type and Other Type); Social Phobia (300.23); Obsessive-Compulsive Disorder (300.3); Posttraumatic Stress Disorder (309.81); Acute Stress Disorder (308.3); Generalized Anxiety Disorder (300.02); Anxiety Disorder Due to a General Medical Condition (293.84); Substance-Induced Anxiety Disorder; and Anxiety Disorder Not Otherwise Specified (300.00).

v) Substance-related disorders for example Substance Use Disorders (including Substance Dependence, Substance Craving and Substance Abuse); Substance-Induced Disorders (including Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders (including Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9)); Amphetamine (or Amphetamine-Like)-Related Disorders (for example Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9)); Caffeine Related Disorders (including Caffeine Intoxication (305.90), Caffeine-Induced Anxiety Disorder, Caffeine-Induced Sleep Disorder and Caffeine-Related Disorder Not Otherwise Specified (292.9)); Cannabis-Related Disorders (including Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9)); Cocaine-Related Disorders (including Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9)); Hallucinogen-Related Disorders (including Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9)); Inhalant-Related Disorders (including Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9)); Nicotine-Related Disorders (including Nicotine Dependence (305.1), Nicotine Withdrawal (292.0) and Nicotine-Related Disorder Not Otherwise Specified (292.9)); Opioid-Related Disorders (including Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9)); Phencyclidine (or Phencyclidine-Like)-Related Disorders (including Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9)); Sedative-, Hypnotic-, or Anxiolytic-Related Disorders (including Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9)); Polysubstance-Related Disorder (including Polysubstance Dependence (304.80)); and Other (or Unknown) Substance-Related Disorders (including Anabolic Steroids, Nitrate Inhalants and Nitrous Oxide).

vi) Sleep disorders for example primary sleep disorders such as Dyssomnias (including Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47)); primary sleep disorders such as Parasomnias (including Nightmare Disorder (307.47), Sleep Terror Disorder (307.46), Sleepwalking Disorder (307.46) and Parasomnia Not Otherwise Specified (307.47)); Sleep Disorders Related to Another Mental Disorder (including Insomnia Related to Another Mental Disorder (307.42) and Hypersomnia Related to Another Mental Disorder (307.44)); Sleep Disorder Due to a General Medical Condition; and Substance-Induced Sleep Disorder (including the subtypes Insomnia Type, Hypersomnia Type, Parasomnia Type and Mixed Type).

vii) Eating disorders such as Anorexia Nervosa (307.1) (including the subtypes Restricting Type and Binge-Eating/Purging Type); Bulimia Nervosa (307.51) (including the subtypes Purging Type and Nonpurging Type); Obesity; Compulsive Eating Disorder; Binge Eating Disorder; and Eating Disorder Not Otherwise Specified (307.50).

viii) Autism Spectrum Disorders including Autistic Disorder (299.00), Asperger's Disorder, Rett's Disorder, Childhood Disintegrative Disorder and Pervasive Developmental Disorder Not Otherwise Specified.

ix) Attention-Deficit/Hyperactivity Disorder (including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9)); Hyperkinetic Disorder; Disruptive Behaviour Disorders such as Conduct Disorder (including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23).

x) Personality Disorders including the subtypes Paranoid Personality Disorder (301.0), Schizoid Personality Disorder (301.20), Schizotypal Personality Disorder (301,22), Antisocial Personality Disorder (301.7), Borderline Personality Disorder (301,83), Histrionic Personality Disorder (301.50), Narcissistic Personality Disorder (301,81), Avoidant Personality Disorder (301.82), Dependent Personality Disorder (301.6), Obsessive-Compulsive Personality Disorder (301.4) and Personality Disorder Not Otherwise Specified (301.9).

xi) Sexual dysfunctions such as Sexual Desire Disorders (including Hypoactive Sexual Desire Disorder (302.71) and Sexual Aversion Disorder (302.79)); sexual arousal disorders (including Female Sexual Arousal Disorder (302.72) and Male Erectile Disorder (302.72)); orgasmic disorders (including Female Orgasmic Disorder (302.73), Male Orgasmic Disorder (302.74) and Premature Ejaculation (302.75)); sexual pain disorder (including Dyspareunia (302.76) and Vaginismus (306.51)); Sexual Dysfunction Not Otherwise Specified (302.70); paraphilias (including Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9)); gender identity disorders (including Gender Identity Disorder in Children (302.6) and Gender Identity Disorder in Adolescents or Adults (302.85)); and Sexual Disorder Not Otherwise Specified (302.9).

The compounds of the invention may also be useful in treating inflammation, pain including inflammatory pain and neuropathic pain, rheumatoid arthritis and sepsis.

In one embodiment, the patient is a human. The term "treatment" includes prophylaxis, where this is appropriate for the relevant condition(s).

In one aspect, the present invention provides a compound of formula (Ia) as hereinbefore described or a salt thereof for use as a medicament. In a further aspect, the invention provides a compound of list B or a salt thereof for use as a medicament.

In one aspect, the present invention provides a compound of formula (I) as hereinbefore described or a salt thereof for use in treating a disease which is associated with a reduction in function of α7 nicotinic acetyl choline receptor. For example, the present invention provides a compound of list A or list B or a salt thereof for use in treating a disease which is associated with a reduction in function of α7 nicotinic acetyl choline receptor.

In one aspect, the present invention provides a compound of formula (I) as hereinbefore described or a salt thereof for use in treating a disease which benefits from positive allosteric modulation of the α7 nicotinic acetyl choline receptor.

In one aspect, the present invention provides a compound of formula (I) as hereinbefore described or a salt thereof for use as a positive allosteric modulator of the α7 nicotinic acetyl choline receptor.

In another aspect, the invention provides a compound of formula (I) as hereinbefore described or a salt thereof for use in the treatment of a psychotic disorder. In one embodiment, the invention provides a compound of formula (I) as hereinbefore described or a salt thereof for use in the treatment of schizophrenia. In one embodiment, the invention provides a compound of formula (I) as hereinbefore described or a salt thereof for use in the treatment of anxiety or depression.

The invention also provides a compound of formula (I) as hereinbefore described or a salt thereof for use in the treatment of cognitive impairment.

The invention also provides a compound of formula (I) as hereinbefore described or a salt thereof for use in the treatment of Alzheimer's disease.

The invention also provides a compound of formula (I) as hereinbefore described or a salt thereof for use in the treatment of pain, for example inflammatory pain or neuropathic pain, especially neuropathic pain.

In another aspect, the invention provides the use of a compound of formula (I) as hereinbefore described or a salt thereof in the manufacture of a medicament for treating a disease which is associated with a reduction in function of α7 nicotinic acetyl choline receptor.

In another aspect, the invention provides the use of a compound of formula (I) as hereinbefore described or a salt thereof in the manufacture of a medicament for use in treating a disease which benefits from positive allosteric modulation of the α7 nicotinic acetyl choline receptor.

In another aspect, the invention provides the use of a compound of formula (I) as hereinbefore described or a salt thereof in the manufacture of a medicament for the positive allosteric modulation of the α7 nicotinic acetyl choline receptor.

In another aspect, the invention provides the use of a compound of formula (I) as hereinbefore described or a salt thereof in the manufacture of a medicament for use in the treatment of a psychotic disorder. In another aspect, the invention provides the use of a compound of formula (I) as hereinbefore described or a salt thereof in the manufacture of a medicament for use in the treatment of schizophrenia. In another aspect, the invention provides the use of a compound of formula (I) as hereinbefore described or a salt thereof in the manufacture of a medicament for use in the treatment of anxiety or depression.

In another aspect, the invention provides the use of a compound of formula (I) as hereinbefore described or a salt thereof in the manufacture of a medicament for use in the treatment of cognitive impairment.

In another aspect, the invention provides the use of a compound of formula (I) as hereinbefore described or a salt thereof in the manufacture of a medicament for use in the treatment of Alzheimer's disease.

In another aspect, the invention provides the use of a compound of formula (I) as hereinbefore described or a salt thereof in the manufacture of a medicament for use in the treatment of pain, for example inflammatory pain or neuropathic pain, especially neuropathic pain.

In another aspect, the invention provides a method of treating a disease which is associated with a reduction in function of α7 nicotinic acetyl choline receptor, which comprises administering to a human in need thereof an effective amount of a compound of formula (I) as hereinbefore described or a salt thereof.

In one aspect, the present invention provides a method of treating a disease which benefits from positive allosteric modulation of the α7 nicotinic acetyl choline receptor, which comprises administering to a human in need thereof an effective amount of a compound of formula (I) as hereinbefore described or a salt thereof.

In one aspect, the present invention provides a method for the positive allosteric modulation of the α7 nicotinic acetyl choline receptor, which comprises administering to a human an effective amount of a compound of formula (I) as hereinbefore described or a salt thereof.

In another aspect, the invention provides a method for use in treating a psychotic disorder, which comprises administering to a human in need thereof an effective amount of a compound of formula (I) as hereinbefore described or a salt thereof.

In one embodiment, the invention provides a method for treating schizophrenia, which comprises administering to a human in need thereof an effective amount of a compound of formula (I) as hereinbefore described or a salt thereof.

In one embodiment, the invention provides a method for treating anxiety or depression, which comprises administering to a human in need thereof an effective amount of a compound of formula (I) as hereinbefore described or a salt thereof.

The invention also provides a method for treating cognitive impairment, which comprises administering to a human in need thereof an effective amount of a compound of formula (I) as hereinbefore described or a salt thereof.

The invention also provides a method for treating Alzheimer's disease, which comprises administering to a human in need thereof an effective amount of a compound of formula (I) as hereinbefore described or a salt thereof.

The invention also provides a method for treating pain, for example inflammatory pain or neuropathic pain, especially neuropathic pain, which comprises administering to a human in need thereof an effective amount of a compound of formula (I) as hereinbefore described or a salt thereof.

In general, compounds of formula (I) or a salt thereof may be administered in doses ranging from about 0.1 mg to about 1000 mg per day, in single or divided doses (i.e., from 1 to 4 doses per day), although variations will necessarily occur depending upon the weight, age and condition of the patient being treated, as well as the particular route of administration chosen. In an embodiment, the dose is administered once daily. In an embodiment, the dosage level is in the range of about 0.1 mg/kg to about 500 mg/kg body weight per day. In a further embodiment, the dosage level is in the range of about 0.1 mg/kg to about 100 mg/kg body weight per day.

The compounds of formula (I) and salts thereof may also be suitable for use in combination with other actives, such as typical and atypical antipsychotics, mood stabilisers, antidepressants, anxiolytics, drugs for extrapyramidal side effects and cognitive enhancers to provide improved treatment of psychotic disorders. In one aspect, the invention provides a combination of a compound of the formula (I) or a salt thereof and a further active ingredient. In one embodiment, the further active ingredient is an additional therapeutic agent The combination therapies of the invention are, for example, administered adjunctively. By adjunctive administration is meant the coterminous or overlapping administration of each of the components in the form of separate pharmaceutical compositions or devices. This regime of therapeutic administration of two or more therapeutic agents is referred to generally by those skilled in the art and herein as adjunctive therapeutic administration; it is also known as add-on therapeutic administration. Any and all treatment regimes in which a patient receives separate but coterminous or overlapping therapeutic administration of a compound of formula (I) or a salt thereof and at least one antipsychotic agent, a mood stabiliser, an antidepressant, an anxiolytic, a drug for extrapyramidal side effects or a cognitive enhancer are within the scope of the current invention. In one embodiment of adjunctive therapeutic administration as described herein, a patient is typically stabilised on a therapeutic administration of one or more of the components for a period of time and then receives administration of another component. The compounds of formula (I) or a salt thereof may be administered as adjunctive therapeutic treatment to patients who are receiving administration of at least one antipsychotic agent, a mood stabiliser, an antidepressant, an anxiolytic, a drug for extrapyramidal side effects or a cognitive enhancer, but the scope of the invention also includes the adjunctive therapeutic administration of at least one antipsychotic agent, a mood stabiliser, an antidepressant, an anxiolytic, a drug for extrapyramidal side effects or a cognitive enhancer to patients who are receiving administration of compounds of formula (I) or a salt thereof.

The combination therapies of the invention may also be administered simultaneously. By simultaneous administration is meant a treatment regime wherein the individual components are administered together, either in the form of a single pharmaceutical composition or device comprising or containing both components, or as separate compositions or devices, each comprising one of the components, administered simultaneously. Such combinations of the separate individual components for simultaneous combination may be provided in the form of a kit-of-parts.

In a further aspect therefore, the invention provides a method of treatment of a psychotic disorder by adjunctive therapeutic administration of a compound of formula (I) or a salt thereof to a patient receiving therapeutic administration of at least one antipsychotic agent. In a further aspect, the invention provides the use of a compound of formula (I) or a salt thereof in the manufacture of a medicament for adjunctive therapeutic administration for the treatment of a psychotic disorder in a patient receiving therapeutic administration of at least one antipsychotic agent. The invention further provides a compound of formula (I) or a salt thereof for use for adjunctive therapeutic administration for the treatment of a psychotic disorder in a patient receiving therapeutic administration of at least one antipsychotic agent.

In a further aspect, the invention provides a method of treatment of a psychotic disorder by adjunctive therapeutic administration of at least one antipsychotic agent to a patient receiving therapeutic administration of a compound of formula (I) or a salt thereof. In a further aspect, the invention provides the use of at least one antipsychotic agent in the manufacture of a medicament for adjunctive therapeutic administration for the treatment of a psychotic disorder in a patient receiving therapeutic administration of a compound of formula (I) or a salt thereof. The invention further provides at least one antipsychotic agent for adjunctive therapeutic administration for the treatment of a psychotic disorder in a patient receiving therapeutic administration of a compound of formula (I) or a salt thereof.

In a further aspect, the invention provides a method of treatment of a psychotic disorder by simultaneous therapeutic administration of a compound of formula (I) or a salt thereof in combination with at least one antipsychotic agent. The invention further provides the use of a combination of a compound of formula (I) or a salt thereof and at least one antipsychotic agent in the manufacture of a medicament for simultaneous therapeutic administration in the treatment of a psychotic disorder. The invention further provides the use of a compound of formula (I) or a salt thereof in the manufacture of a medicament for simultaneous therapeutic administration with at least one antipsychotic agent in the treatment of a psychotic disorder. The invention further provides a compound of formula (I) or a salt thereof for use for simultaneous therapeutic administration with at least one antipsychotic agent in the treatment of a psychotic disorder. The invention further provides the use of at least one antipsychotic agent in the manufacture of a medicament for simultaneous therapeutic administration with a compound of formula (I) or a salt thereof in the treatment of a psychotic disorder.

In a further aspect, the invention provides a kit-of-parts for use in the treatment of a psychotic disorder comprising a first dosage form comprising a compound of formula (I) or a salt thereof and one or more further dosage forms each comprising an antipsychotic agent for simultaneous therapeutic administration.

In another aspect, the invention provides a method of treatment of a psychotic disorder by adjunctive therapeutic administration of a compound of the present invention to a patient receiving therapeutic administration of an active ingredient selected from the group consisting of: a mood stabiliser, an antidepressant, an anxiolytic, a drug for extrapyramidal side effects and a cognitive enhancer.

In a further aspect, the invention provides the use of a compound of the present invention in the manufacture of a medicament for adjunctive therapeutic administration for the treatment of a psychotic disorder in a patient receiving therapeutic administration of an active ingredient selected from the group consisting of: a mood stabiliser, an antidepressant, an anxiolytic, a drug for extrapyramidal side effects and a cognitive enhancer.

The invention also provides the use of a compound of the present invention in adjunctive therapeutic administration for the treatment of a psychotic disorder in a patient receiving therapeutic administration of an active ingredient selected from the group consisting of: a mood stabiliser, an antidepressant, an anxiolytic, a drug for extrapyramidal side effects and a cognitive enhancer.

The invention further provides the use of a compound of the present invention for use for adjunctive therapeutic administration for the treatment of a psychotic disorder in a patient receiving therapeutic administration of an active ingredient selected from the group consisting of: a mood stabiliser, an antidepressant, an anxiolytic, a drug for extrapyramidal side effects and a cognitive enhancer.

In a further aspect, the invention provides a method of treatment of a psychotic disorder by adjunctive therapeutic administration of an active ingredient selected from the group consisting of: a mood stabiliser, an antidepressant, an anxiolytic, a drug for extrapyramidal side effects and a cognitive enhancer to a patient receiving therapeutic administration of a compound of the present invention.

In a further aspect, the invention provides the use of an active ingredient selected from the group consisting of: a mood stabiliser, an antidepressant, an anxiolytic, a drug for extrapyramidal side effects and a cognitive enhancer in the manufacture of a medicament for adjunctive therapeutic administration for the treatment of a psychotic disorder in a patient receiving therapeutic administration of a compound of the present invention.

The invention also provides the use of an active ingredient selected from the group consisting of: a mood stabiliser, an antidepressant, an anxiolytic, a drug for extrapyramidal side effects and a cognitive enhancer for adjunctive therapeutic administration for the treatment of a psychotic disorder in a patient receiving therapeutic administration of a compound of the present invention.

In a further aspect, the invention provides a method of treatment of a psychotic disorder by simultaneous therapeutic administration of a compound of the present invention in combination with an active ingredient selected from the group consisting of: a mood stabiliser, an antidepressant, an anxiolytic, a drug for extrapyramidal side effects and a cognitive enhancer.

The invention further provides the use of a combination of a compound of the present invention and an active ingredient selected from the group consisting of: a mood stabiliser, an antidepressant, an anxiolytic, a drug for extrapyramidal side effects and a cognitive enhancer in the manufacture of a medicament for simultaneous therapeutic administration in the treatment of a psychotic disorder.

The invention further provides the use of a combination of a compound of the present invention and an active ingredient selected from the group consisting of: a mood stabiliser, an antidepressant, an anxiolytic, a drug for extrapyramidal side effects and a cognitive enhancer for simultaneous therapeutic administration in the treatment of a psychotic disorder.

The invention further provides the use of a compound of the present invention in the manufacture of a medicament for simultaneous therapeutic administration with an active ingredient selected from the group consisting of: a mood stabiliser, an antidepressant, an anxiolytic, a drug for extrapyramidal side effects and a cognitive enhancer in the treatment of a psychotic disorder.

The invention further provides the use of a compound of the present invention for simultaneous therapeutic administration with an active ingredient selected from the group consisting of: a mood stabiliser, an antidepressant, an anxiolytic, a drug for extrapyramidal side effects and a cognitive enhancer in the treatment of a psychotic disorder.

The invention further provides a compound of the present invention for use for simultaneous therapeutic administration with an active ingredient selected from the group consisting of: a mood stabiliser, an antidepressant, an anxiolytic, a drug for extrapyramidal side effects and a cognitive enhancer in the treatment of a psychotic disorder.

The invention further provides the use of an active ingredient selected from the group consisting of: a mood stabiliser, an antidepressant, an anxiolytic, a drug for extrapyramidal side effects and a cognitive enhancer in the manufacture of a medicament for simultaneous therapeutic administration with a compound of the present invention in the treatment of a psychotic disorder.

The invention further provides the use of an active ingredient selected from the group consisting of: a mood stabiliser, an antidepressant, an anxiolytic, a drug for extrapyramidal side effects and a cognitive enhancer for simultaneous therapeutic administration with a compound of the present invention in the treatment of a psychotic disorder.

In a further aspect, the invention provides a kit-of-parts for use in the treatment of a psychotic disorder comprising a first dosage form comprising a compound of the present invention and one or more further dosage forms each comprising an active ingredient selected from the group consisting of: a mood stabiliser, an antidepressant, an anxiolytic, a drug for extrapyramidal side effects and a cognitive enhancer for simultaneous therapeutic administration.

Examples of antipsychotic drugs that may be useful in the present invention include, but are not limited to: sodium channel blockers; mixed 5HT/dopamine receptor antagonists; mGluR5 positive modulators; D3 antagonists; 5HT6 angatonists; nicotinic alpha-7 modulators; glycine transporter GlyT1 inhibitors; D2 partial agonist/D3 antagonist/H3 antagonists; AMPA modulators; NK3 antagonists such as osanetant and talnetant; an atypical antipsychotic, for example clozapine, olanzapine, risperidone, quetiapine, aripirazole, ziprasidone and amisulpride; butyrophenones, such as haloperidol, pimozide, and droperidol; phenothiazines, such as chlorpromazine, thioridazine, mesoridazine, trifluoperazine, perphenazine, fluphenazine, thiflupromazine, prochlorperazine, and acetophenazine; thioxanthenes, such as thiothixene and chlorprothixene; thienobenzodiazepines; dibenzodiazepines; benzisoxazoles; dibenzothiazepines; imidazolidinones; benzisothiazolyl-piperazines; triazine such as lamotrigine; dibenzoxazepines, such as loxapine; dihydroindolones, such as molindone; aripiprazole; and derivatives thereof that have antipsychotic activity.

Thus, specific examples of selected antipsychotic drugs that may be suitable for use in the present invention are as follows: clozapine; olanzapine; ziprasidone; risperidone; quetiapine fumarate; sertindole; amisulpride; haloperidol; haloperidol decanoate; haloperidol lactate; chlorpromazine; fluphenazine; fluphenazine decanoate; fluphenazine enanthate; fluphenazine hydrochloride; thiothixene; thiothixene hydrochloride; trifluoperazine (10-[3-(4-methyl-1-piperazinyl)propyl]-2-(trifluoromethyl)phenothiazine dihydrochloride; perphenazine; perphenazine and amitriptyline hydrochloride; thioridazine; molindone; molindone hydrochloride; loxapine; loxapine hydrochloride; and loxapine succinate. Furthermore, benperidol, perazine or melperone may be used.

Other suitable antipsychotic drugs include promazine, triflurpromazine, chlorprothixene, droperidol, acetophenazine, prochlorperazine, methotrimeprazine, pipotiazine, iloperidone, pimozide and flupenthixol.

In one further aspect of the invention, suitable antipsychotic agents include olanzapine, risperidone, quetiapine, aripiprazole, haloperidol, clozapine, ziprasidone, talnetant and osanetant.

Mood stabilisers which may be used in the therapy of the present invention include lithium, sodium valproate/valproic acid/divalproex, carbamazepine, lamotrigine, gabapentin, topiramate, oxcarbazepine and tiagabine.

Antidepressant drugs which may be used in the therapy of the present invention include serotonin antagonists, CRF-1 antagonists, Cox-2 inhibitor/SSRI dual antagonists; dopamine/noradrenaline/serotonin triple reuptake inhibitors; NK1 antagonists; NK1 and NK2 dual antagonists; NK1/SSRI dual antagonists; NK2 antagonists; serotonin agonists (such as rauwolscine, yohimbine and metoclopramide); serotonin reuptake inhibitors (such as citalopram, escitalopram, fluoxetine, fluvoxamine, femoxetine, indalpine, zimeldine, paroxetine and sertraline); dual serotonin/noradrenaline reuptake inhibitors (such as venlafaxine, reboxetine, duloxetine and milnacipran); Noradrenaline reuptake inhibitors (such as reboxetine); tricyclic antidepressants (such as amitriptyline, clomipramine, imipramine, maprotiline, nortriptyline and trimipramine); monoamine oxidase inhibitors (such as isocarboxazide, moclobemide, phenelzine and tranylcypromine); 5HT3 antagonists (such as example ondansetron and granisetron); and others (such as bupropion, amineptine, radafaxine, mianserin, mirtazapine, nefazodone and trazodone).

Anxiolytics which may be used in the therapy of the present invention include V1b antagonists, $5HT_7$ antagonists and benzodiazepines such as alprazolam and lorazepam.

Drugs for extrapyramidal side effects which may be used in the therapy of the present invention include anticholinergics (such as benztropine, biperiden, procyclidine and trihexyphenidyl), antihistamines (such as diphenhydramine) and dopaminergics (such as amantadine).

Cognitive enhancers which may be used in the therapy of the present invention include example cholinesterase inhibitors (such as tacrine, donepezil, rivastigmine and galantamine), H3 antagonists and muscarinic M1 agonists (such as cevimeline).

In one embodiment, the active ingredient for use in combination with a compound of the present invention, is an atypical antipsychotic, for example clozapine, olanzapine, risperidone, quetiapine, aripirazole, ziprasidone or amisulpride.

In one embodiment, the active ingredient for use in combination with a compound of the present invention is a typical antipsychotic, for example chlorpromazine, thioridazine, mesoridazine, fluphenazine, perphenazine, prochlorperazine, trifluoperazine, thiothixine, haloperidol, thiflurpromazine, pimozide, droperidol, chlorprothixene, molindone or loxapine.

In another embodiment, the active ingredient for use in combination with a compound of the present invention is a mood stabiliser, for example lithium, sodium valproate/valproic acid/divalproex, carbamazepine, lamotrigine, gabapentin, topiramate, oxcarbazepine or tiagabine.

In another embodiment, the active ingredient for use in combination with a compound of the present invention is an antidepressant, for example a serotonin agonist (such as rauwolscine, yohimbine or metoclopramide); a serotonin reuptake inhibitor (such as citalopram, escitalopram, fluoxetine, fluvoxamine, femoxetine, indalpine, zimeldine, paroxetine or sertraline); a dual serotonin/noradrenaline reuptake inhibitor (such as venlafaxine, reboxetine, duloxetine or milnacipran); a noradrenaline reuptake inhibitors (such as reboxetine); a tricyclic antidepressants (such as amitriptyline, clomipramine, imipramine, maprotiline, nortriptyline or trimipramine); a monoamine oxidase inhibitor (such as isocarboxazide, moclobemide, phenelzine or tranylcypromine); or other (such as bupropion, amineptine, radafaxine, mianserin, mirtazapine, nefazodone or trazodone). In another embodiment, the active ingredient for use in combination with a compound of the present invention is an anxiolytic, for example a benzodiazepine such as alprazolam or lorazepam.

For use in medicine, the compounds of the present invention are usually administered as a standard pharmaceutical composition. The present invention therefore provides in a further aspect a pharmaceutical composition comprising a compound of formula (Ia) as hereinbefore described or a salt thereof and a pharmaceutically acceptable carrier or excipient. The pharmaceutical composition can be for use in the treatment of any of the conditions described herein. The present invention therefore provides in a further aspect a pharmaceutical composition comprising a compound of formula (I) as hereinbefore described or a salt thereof for use in the treatment of any of the conditions described herein. In one embodiment, the pharmaceutical composition of the invention, further comprises an additional therapeutic agent.

The compounds of the invention may be administered by any convenient method, for example by oral, parenteral (e.g. intravenous), buccal, sublingual, nasal, rectal or transdermal administration and the pharmaceutical compositions adapted accordingly.

The compounds of the invention which are active when given orally can be formulated as liquids or solids, for example syrups, suspensions or emulsions, tablets, capsules and lozenges.

A liquid formulation will generally consist of a suspension or solution of the compound or salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

The composition may be in unit dose form such as a tablet, capsule or ampoule. Each dosage unit for oral administration may contain, for example, from 1 to 500 mg (and for parenteral administration contains, for example, from 0.1 to 50 mg) of a compound of the formula (I) or a salt thereof calculated as the free base. In an embodiment the unit dose for oral administration contains from 50 to 450 mg. In a further embodiment the unit dose contains from 100 to 400 mg.

In order to obtain consistency of adjunctive administration, the compositions of each of the components, or of the combination of the components is, for example, in the form of a unit dose.

The Examples set forth below are illustrative of the present invention and are not intended to limit, in any way, the scope of the present invention.

EXAMPLES

The preparation of a number of compounds of the invention are exemplified below.

Compounds of the invention and intermediates are named using ACD/Name PRO6.02 chemical naming software (Advanced Chemistry Development Inc., Toronto, Ontario, M5H2L3, Canada).

ABBREVIATIONS

LC/MS Liquid Chromatography/Mass Spectrometry
NMR Nuclear Magnetic Resonance
THF tetrahydrofuran
DMSO dimethylsulfoxide
DMF N,N-dimethylformamide
MDAP Mass-directed auto-preparation
min minutes
Me methyl
Et ethyl
ether diethyl ether
BINAP 2,2'-bis(diphenylphosphino)-1,1'-binaphthyl Starting materials were obtained from commercial suppliers (such as Aldrich, Alfa Aesar, Apollo Scientific, Avocado, Frontier Scientific Inc. or Lancaster) and used without further purification unless otherwise stated. Flash chromatography was carried out using pre-packed Isolute Flash™ or Biotage™ silica-gel columns as the stationary phase and analytical grade solvents as the eluent unless otherwise stated.

NMR spectra were obtained at 298K, 303.2K or 300K, at the frequency stated using either a Bruker™ DPX400 or AV400 machine and run as a dilute solution of the deuterated solvent stated. All NMR spectra were reference to tetramethylsilane (TMS $\delta_H 0$, $\delta_C 0$). All coupling constants are reported in hertz (Hz), and multiplicities are labelled s (singlet), bs, (broad singlet), d (doublet), t (triplet), q (quartet), dd (doublet of doublets), dt (doublet of triplets) and m (multiplet).

Purification

A number of the compounds were purified using a Mass Directed Auto-Purification System (MDAP) incorporating HPLC techniques and an appropriate mass spectrometer such as the Waters ZQ mass spectrometer.

Intermediate 1:
N,2-Dimethyl-N-(methyloxy)-3-furancarboxamide

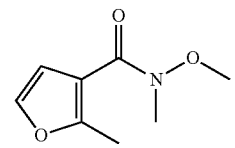

A mixture of methoxymethylamine hydrochloride (5.85 g, 60.0 mmol) and triethylamine (16.73 ml, 120 mmol) in dichloromethane (100 ml) was stirred at 0° C. A solution of 2-methyl-3-furancarbonyl chloride (7.23 g, 50 mmol) in dichloromethane (20 ml) was added and the reaction mixture was stirred at room temperature for 30 minutes. The reaction mixture was diluted with water. The organic layer was separated, washed with saturated sodium hydrogen carbonate solution, water and brine, dried and evaporated to give the title compound as an oil (6.7 g, 79%); LC/MS [M+H]⁺=170.

Intermediate 2: 1-(2-Methyl-3-furanyl)-2-(4-pyridinyl)ethanone

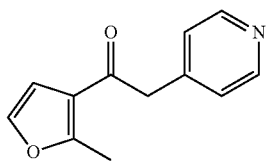

To a solution of lithium diisopropylamide (2M solution in THF/heptane/ethylbenzene) (12.00 ml, 24.00 mmol) in tetrahydrofuran (20 ml) at −78° C. under argon was added 4-picoline (1.946 ml, 20 mmol). The reaction mixture was stirred at −78° C. for 15 minutes and a solution of N,2-dimethyl-N-(methyloxy)-3-furancarboxamide (3.38 g, 20.00 mmol) in tetrahydrofuran (5 ml) was added dropwise. The solution was allowed to warm to room temperature over 2 hours. Brine was added and the mixture was extracted with dichloromethane. The organic layer was separated and washed with saturated sodium hydrogen carbonate solution, water and brine, dried and evaporated to give the title compound as a solid (3.72 g, 92%). LC/MS [M+H]$^+$=202.

Intermediate 3: 3-(Dimethylamino)-1-(2-methyl-3-furanyl)-2-(4-pyridinyl)-2-propen-1-one

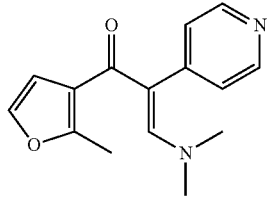 [SMILES: Cc1occc1C(=O)/C(=C/N(C)C)c1ccncc1]

A mixture of 1-(2-methyl-3-furanyl)-2-(4-pyridinyl)ethanone (1.006 g, 5 mmol) in N,N-dimethylformamide dimethyl acetal (0.664 ml, 5 mmol) was heated at 100° C. for 2 hours. The mixture was cooled to room temperature and the solvent was evaporated. The residue was partitioned between ethyl acetate and water. The organic phase was separated, washed with water and brine, dried and evaporated to give the title compound as an oil (1.1 g, 86%). LC/MS [M+H]$^+$=257.

Intermediate 4:
3-Methyl-1-piperidinecarboximidamide hydrochloride

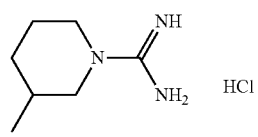

A mixture of 3-methylpiperidine (2.347 ml, 20 mmol), diisopropylethylamine (3.49 ml, 20.00 mmol) and 1H-1,2,4-triazole-1-carboximidamide hydrochloride (2.444 g, 22.00 mmol) in N,N-dimethylformamide (10 ml) was stirred at room temperature overnight. Ether (50 ml) was added to the reaction mixture and the mixture was stirred at room temperature for 10 minutes. The ether layer was separated and DMF layer was stirred with ether (50 ml) at 5° C. (ice water bath) for 10 minutes and the ether layer was separated from the residue. Ether (20 ml) was added to the residue and the mixture was stirred at 5° C. The resulting solid was triturated with ether, collected, washed with ether and dried to give the title compound as a colourless solid (2.95 g, 83%). LC/MS [M+H]$^+$=142.

Intermediate 5:
1-(2-Methyl-3-furanyl)-2-(3-pyridinyl)ethanone

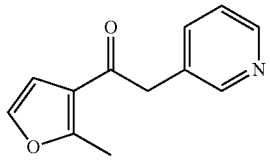

Lithium diisopropylamide (2M solution in THF/heptane/ethylbenzene) (6.00 ml, 12.00 mmol) was added to a stirred solution of 3-picoline (0.584 ml, 6.00 mmol) in tetrahydrofuran (10 ml) at 0° C. under argon. After 30 minutes, a solution of N,2-dimethyl-N-(methyloxy)-3-furancarboxamide (1.015 g, 6 mmol) in tetrahydrofuran (2 ml) was added dropwise and the reaction mixture was stirred at 0° C. for 1 hour. Water was added and the mixture was extracted with dichloromethane. The organic layer was separated and washed with saturated sodium hydrogen carbonate solution, water and brine, dried and evaporated to give the title compound as an oil (1.21 g) which was used crude in the next step. LC/MS [M+H]$^+$=202.

Intermediate 6: 3-(Dimethylamino)-1-(2-methyl-3-furanyl)-2-(3-pyridinyl)-2-propen-1-one

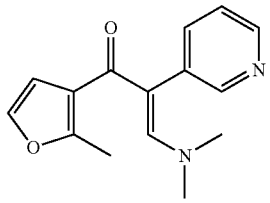 [SMILES: Cc1occc1C(=O)/C(=C/N(C)C)c1cccnc1]

A mixture of 1-(2-methyl-3-furanyl)-2-(3-pyridinyl)ethanone (1207 mg, 6 mmol) in N,N-dimethylformamide dimethyl acetal (797 μl, 6.00 mmol) was heated at 100° C. for 2 hours. The mixture was cooled to room temperature and the solvent was evaporated. The residue was partitioned between ethyl acetate and water. The organic phase was separated, washed with water and brine, dried and evaporated to give the title compound as an orange oil (750 mg, 49%). LC/MS [M+H]$^+$=257.

Intermediate 7: 1-(2-Methyl-3-furanyl)-2-(2-methyl-4-pyridinyl)ethanone

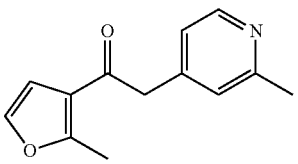 [SMILES: Cc1cc(CC(=O)c2ccoc2C)ccn1]

A solution of lithium diisopropylamide (2M solution in THF/heptane/ethylbenzene) (10.00 ml, 20.00 mmol) in tetrahydrofuran (20 ml) was stirred at −30° C. under argon. A solution of 2,4-lutidine (2.312 ml, 20.00 mmol) in tetrahydrofuran (5 ml) was added dropwise at −30° C. and the reaction mixture was stirred at −10° C. for 1 hour and then cooled to −78° C. A solution of N,2-dimethyl-N-(methyloxy)-3-furancarboxamide (3.38 g, 20 mmol) in tetrahydrofuran (5 ml) was added dropwise maintaining the internal temperature below −60° C. The mixture was stirred at −78° C. for 1 hour and then allowed to warm to room temperature. Water was added and the reaction mixture was extracted with dichloromethane. The organic layer was separated and washed with saturated sodium hydrogen carbonate solution, water and brine, dried and evaporated. The residue was purified by silica gel chromatography eluting with 25-50% ethyl acetate in isohexane to give the title compound as a solid (2.56 g, 60%). LC/MS $[M+H]^+=216$.

Intermediate 8: 3-(Dimethylamino)-1-(2-methyl-3-furanyl)-2-(2-methyl-4-pyridinyl)-2-propen-1-one

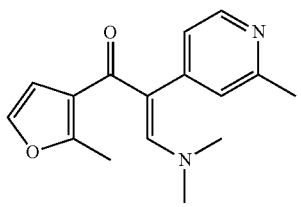 [SMILES: Cc1cc(/C(=C\N(C)C)C(=O)c2ccoc2C)ccn1]

A mixture of 1-(2-methyl-3-furanyl)-2-(2-methyl-4-pyridinyl)ethanone (0.430 g, 2.000 mmol) in N,N-dimethylformamide dimethyl acetal (0.266 ml, 2 mmol) was heated at 100° C. for 2 hours. The mixture was cooled to room temperature and the solvent was evaporated to give the title compound (540 mg) which was used crude in the next step. LC/MS $[M+H]^+=271$.

Intermediate 9: 1-Piperidinecarboximidamide hydrochloride

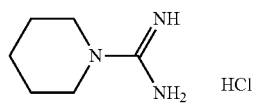

A mixture of piperidine (4.95 ml, 50 mmol), diisopropylethylamine (8.73 ml, 50.0 mmol) and 1H-1,2,4-triazole-1-carboximidamide hydrochloride (6.11 g, 55.0 mmol) in N,N-dimethylformamide (20 ml) was stirred at room temperature over the weekend. Ether (50 ml) was added to the reaction mixture and the mixture was stirred at room temperature for 10 minutes. The ether layer was separated and DMF layer was stirred with ether (50 ml) at 5° C. (ice water bath) for 10 minutes and the ether layer was separated from the residue. Ether (30 ml) was added to the residue and the mixture was stirred at 5° C. The resulting solid was triturated with ether, collected, washed with ether and dried to give the title compound as a colourless solid (3.55 g, 43%). LC/MS $[M+H]^+=128$.

Intermediate 10: 2,6-Dimethyl-4-morpholinecarboximidamide hydrochloride

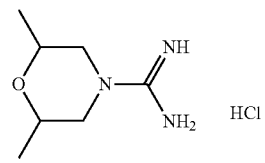

A mixture of 2,6-dimethylmorpholine (6.16 ml, 50.0 mmol) (Fluka, a 2.5:1 mixture of cis:trans isomers), diisopropylethylamine (8.73 ml, 50.0 mmol) and 1H-1,2,4-triazole-1-carboximidamide hydrochloride (6.11 g, 55 mmol) in N,N-dimethylformamide (20 ml) was stirred at room temperature for 24 hours. The suspension was diluted with ether (50 ml) and the reaction mixture was stirred at room temperature for 10 minutes. The ether layer was decanted off. Ether (50 ml) was added and the process repeated twice. The solid was collected, washed with ether and dried to give the title compound as a colourless solid (7.1 g, 73%) as a 2.3:1 mixture of cis:trans isomers. LC/MS $[M+H]^+=158$.

Intermediate 11: 1-(2-Methyl-3-furanyl)-2-(2-pyridinyl)ethanone

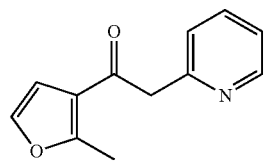

To a solution of lithium diisopropylamide (2M solution in THF/heptane/ethylbenzene) (3.60 ml, 7.20 mmol) in tetrahydrofuran (10 ml) at −78° C. under argon was added 2-picoline (0.593 ml, 6.00 mmol). The reaction mixture was stirred at −78° C. for 15 minutes and a solution of N,2-dimethyl-N-(methyloxy)-3-furancarboxamide (1.015 g, 6 mmol) in tetrahydrofuran (2 ml) was added dropwise. The solution was allowed to warm to room temperature over 1 hour. Brine was added and the mixture was extracted with dichloromethane. The organic layer was separated and washed with saturated sodium hydrogen carbonate solution, water and brine, dried and evaporated to give the title compound as an oil which was used in the next step (1.3 g). LC/MS $[M+H]^+=202$.

Intermediate 12: 3-(Dimethylamino)-1-(2-methyl-3-furanyl)-2-(2-pyridinyl)-2-propen-1-one

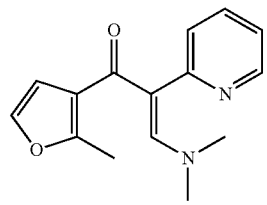 [SMILES: Cc1occc1C(=O)/C(=C/N(C)C)c1ccccn1]

A mixture of 1-(2-methyl-3-furanyl)-2-(2-pyridinyl)ethanone (1.207 g, 6 mmol) in N,N-dimethylformamide dimethyl acetal (0.797 ml, 6.00 mmol) was heated at 100° C. for 2 hours. The mixture was cooled to room temperature and the solvent was evaporated. The residue was partitioned between ethyl acetate and water. The organic phase was separated, washed with water and brine, dried and evaporated to give the title product as a dark orange oil which was used in the next step (1.1 g, 72%). LC/MS [M+H]$^+$=257.

Intermediate 13:
Hexahydro-1H-azepine-1-carboximidamide hydrochloride

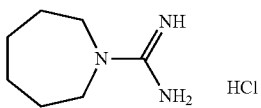

A mixture of hexahydro-1H-azepine (5.63 ml, 50.0 mmol), diisopropylethylamine (8.73 ml, 50.0 mmol) and 1H-1,2,4-triazole-1-carboximidamide hydrochloride (6.11 g, 55 mmol) in N,N-dimethylformamide (20 ml) was stirred at room temperature over the weekend. Ether (100 ml) was added to the reaction mixture and the mixture was stirred at room temperature for 10 minutes. The ether was decanted from the solid residue. The residue was stirred with ether (50 ml) at 5° C. (ice water bath) for 10 minutes and the ether layer was separated from the residue. Ether (50 ml) was added to the residue and the mixture was stirred at 5° C. The resulting solid was collected, washed with ether and dried to give the title compound as a colourless solid (6.8 g, 77%). LC/MS [M+H]$^+$=142.

Intermediate 14: cis-4-(6-Chloro-2-pyrazinyl)-2,6-dimethylmorpholine

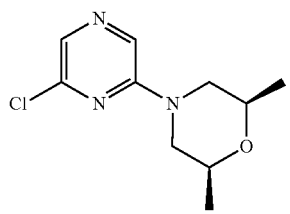

cis-2,6-Dimethylmorpholine (0.850 g, 7.38 mmol) was added to a suspension of 2,6-dichloropyrazine (1 g, 6.71 mmol) and potassium carbonate (2.78 g, 20.14 mmol) in anhydrous acetonitrile (50 mL). After addition, the reaction mixture was stirred at 90° C. for 3 hours. Crude LCMS showed desired product can be seen and no starting material left, so the reaction mixture was diluted with ethyl acetate (100 mL) and water (50 mL). The organic layer was separated and the aqueous layer was extracted with ethyl acetate (2×100 mL). The combined organic layer was dried (sodium sulfate), filtered and concentrated under reduced pressure. The residue was dissolved in dichloromethane (~10 ml) and purified on silica by a Biotage SP4 chromatographic system (40+M cartridge, eluted with 0-100% ethyl acetate in isohexanes). Fractions containing the pure product were combined and concentrated under reduced pressure to give the title compound as a white solid (742 mg, 3.10 mmol, 46.1% yield). LC/MS [M+H]$^+$=228/230.

Intermediate 15: cis-2,6-Dimethyl-4-[6-(2-methyl-3-furanyl)-2-pyrazinyl]morpholine

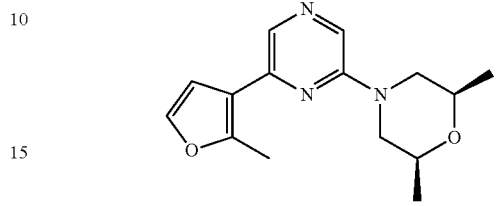

4,4,5,5-Tetramethyl-2-(2-methyl-3-furanyl)-1,3,2-dioxaborolane (567 mg, 2.72 mmol) was added to a solution of cis-4-(6-chloro-2-pyrazinyl)-2,6-dimethylmorpholine (620 mg, 2.72 mmol) in a mixture of 1,4-dioxane (17 mL), water (2.83 mL) and sodium carbonate (577 mg, 5.45 mmol). The solution was degassed using argon gas and then charged with tetrakis(triphenylphosphine)palladium(0) (315 mg, 0.272 mmol). After addition, the reaction mixture was stirred and heated in the microwave at 100° C. for 1 hour. Crude LCMS shows desired product and starting material so the reaction mixture was stirred and heated for a further 1 hour at 100° C. in the microwave. Crude LCMS shows desired product and no starting material can be seen. The reaction mixture washed with ethyl acetate (200 mL), water (100 mL), filtered and then evaporated to dryness. The residue was dissolved in dichloromethane (~5 ml) and purified on silica by a Biotage SP4 chromatographic system (40+M cartridge, eluted with 0-50% ethyl acetate in isohexanes). Fractions containing pure product were combined and concentrated under reduced pressure to give the title compound (441 mg, 1.533 mmol, 56.3% yield). LC/MS [M+H]$^+$=274.

Intermediate 16: cis-4-[5-bromo-6-(2-methyl-3-furanyl)-2-pyrazinyl]-2,6-dimethylmorpholine

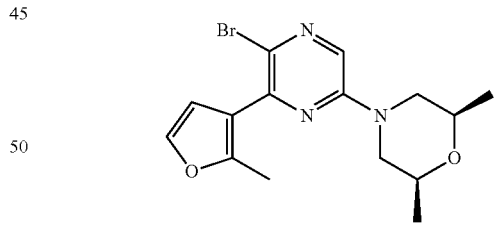

N-Bromosuccinimide (272 mg, 1.529 mmol) was added portionwise to a solution of cis-2,6-dimethyl-4-[6-(2-methyl-3-furanyl)-2-pyrazinyl]morpholine (418 mg, 1.529 mmol) in chloroform (13 mL) at 0° C. The reaction was stirred at 0° C. for 1 hour. Crude LC/MS shows desired product can be seen and no starting material left, so reaction mixture was diluted with ethyl acetate (20 mL) and washed with water (50 mL), brine (50 mL), water (50 mL) and brine (50 mL). The organic layer was dried (sodium sulfate), filtered and concentrated under reduced pressure. The residue was dissolved in dichloromethane (~5 mL) and purified on silica by a Biotage SP4 chromatographic system (40+M cartridge, eluted with 0-100% ethyl acetate in isohexanes). Fractions containing pure product were combined and concentrated under reduced pressure to give the title compound (210 mg, 0.566 mmol, 37.0% yield). LC/MS [M+H]$^+$=352/354.

Intermediate 17: cis-4-(4-Chloro-2-pyridinyl)-2,6-dimethylmorpholine

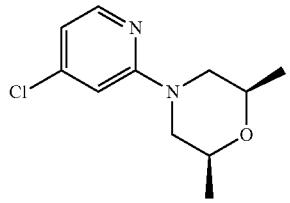

cis-2,6-Dimethylmorpholine (2.029 g, 17.62 mmol) was added to a suspension of 2,4-dichloropyridine (2.37 g, 16.01 mmol) and potassium carbonate (6.64 g, 48.0 mmol) in anhydrous acetonitrile (120 mL). After addition, the reaction mixture was stirred at 100° C. overnight. Crude LC/MS showed starting material and desired product so cis-2,6-dimethylmorpholine (0.500 equivalents) was added to the reaction mixture and then stirred and heated at 100° C. overnight. Crude LC/MS showed starting material and desired product so cis-2,6-dimethylmorpholine (0.500 equivalents) was added to the reaction mixture and then stirred and heated at 100° C. overnight. Crude LC/MS showed starting material and desired product so cis-2,6-dimethylmorpholine (0.500 equivalents) was added to the reaction mixture and then stirred and heated at 100° C. overnight. Crude LCMS showed desired product can be seen and no starting material left, so the reaction mixture was diluted with ethyl acetate (100 mL) and water (50 mL). The organic layer was separated and the aqueous layer was extracted with ethyl acetate (2×100 mL). The combined organic layer was dried (sodium sulfate), filtered and concentrated under reduced pressure. The residue was dissolved in dichloromethane (~10 ml) and purified on silica by a Biotage SP4 chromatographic system (40+M cartridge, eluted with 0-100% ethyl acetate in isohexanes).

Fractions containing pure product were combined and concentrated under reduced pressure to give the title compound as a colourless oil (1 g, 4.15 mmol, 25.9% yield). LC/MS [M+H]$^+$=227/229.

Intermediate 18: cis-2,6-Dimethyl-4-[4-(2-methyl-3-furanyl)-2-pyridinyl]morpholine

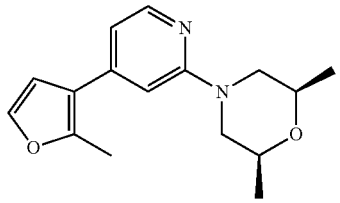 [SMILES: Cc1occc1-c1ccnc(N2C[C@@H](C)O[C@@H](C)C2)c1]

4,4,5,5-Tetramethyl-2-(2-methyl-3-furanyl)-1,3,2-dioxaborolane (0.918 g, 4.41 mmol) was added to a solution of cis-4-(4-chloro-2-pyridinyl)-2,6-dimethylmorpholine (1 g, 4.41 mmol) in a mixture of 1,4-dioxane (17 mL), water (2.83 mL) and sodium carbonate (0.935 g, 8.82 mmol). The solution was degassed using argon gas and then charged with tetrakis(triphenylphosphine)palladium(0) (0.510 g, 0.441 mmol). After addition, the reaction mixture was stirred and heated in the microwave at 100° C. for 4 hours. Crude LC/MS showed desired product and no starting material can be seen. The reaction mixture was washed with ethyl acetate (200 mL), water (100 mL), filtered and then evaporated to dryness. The residue was dissolved in dichloromethane (~10 ml) and purified on silica by a Biotage SP4 chromatographic system (40+M cartridge, eluted with 0-50% ethyl acetate in isohexanes). Fractions containing pure product were combined and concentrated under reduced pressure to give the title compound (336 mg, 1.172 mmol, 26.6% yield). LC/MS [M+H]$^+$=273.

Intermediate 19: cis-4-[5-Bromo-4-(2-methyl-3-furanyl)-2-pyridinyl]-2,6-dimethylmorpholine

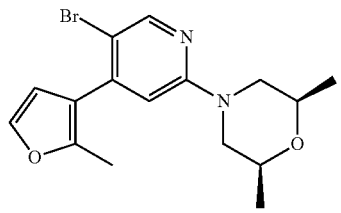 [SMILES: Cc1occc1-c1cc(N2C[C@@H](C)O[C@@H](C)C2)ncc1Br]

N-Bromosuccinimide (133 mg, 0.749 mmol) was added portionwise to a solution of cis-2,6-dimethyl-4-[4-(2-methyl-3-furanyl)-2-pyridinyl]morpholine (204 mg, 0.749 mmol) in chloroform (6 mL) at 0° C. The reaction was stirred at 0° C. for 1 hour. Crude LC/MS showed desired product can be seen and no starting material left, so the reaction mixture was diluted with ethyl acetate and washed with water, brine, water and brine. The organic layer was dried (sodium sulfate), filtered and concentrated under reduced pressure. The residue was dissolved in dichloromethane (~5 ml) and purified on silica by a Biotage SP4 chromatographic system (25+M cartridge, eluted with 0-50% ethyl acetate in isohexanes). Fractions containing pure product were combined and concentrated under reduced pressure to give the title compound (295 mg, 0.798 mmol, 107% yield) as a colourless oil. LC/MS [M+H]$^+$=351/353.

Intermediate 20: cis-4-(6-Bromo-2-pyridinyl)-2,6-dimethylmorpholine

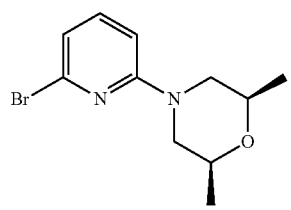

cis-2,6-Dimethylmorpholine (0.535 g, 4.64 mmol) was added to a suspension of 2,6-dibromopyridine (1 g, 4.22 mmol) and potassium carbonate (1.750 g, 12.66 mmol) in anhydrous acetonitrile (35 mL). After addition, the reaction mixture was stirred at 120° C. overnight. Crude LC/MS showed starting material and desired product so cis-2,6-dimethylmorpholine (185 mg, 1.61 mmol) was added to the reaction mixture which was then stirred at 120° C. overnight. Crude LC/MS showed desired product can be seen and no starting material left, so the reaction mixture was diluted with ethyl acetate (100 mL) and water (50 mL). The organic layer was separated and the aqueous layer was extracted with ethyl acetate (2×100 mL). The combined organic layers were dried (sodium sulfate), filtered and concentrated under reduced pressure. The residue was dissolved in dichloromethane (~10 ml) and purified on silica by a Biotage SP4 chromatographic system (40+M cartridge, eluted with 0-100% ethyl acetate in isohexanes). Fractions containing pure product were combined and concentrated under reduced pressure to give the title compound as a colourless oil (705 mg, 2.340 mmol, 55.4% yield). LC/MS [M+H]$^+$=271/273.

Intermediate 21: cis-2,6-Dimethyl-4-[6-(2-methyl-3-furanyl)-2-pyridinyl]morpholine

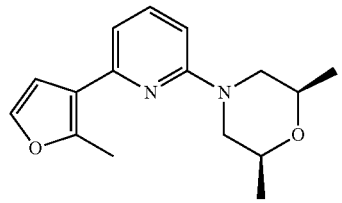 [SMILES: Cc1occc1-c1cccc(N2C[C@@H](C)O[C@@H](C)C2)n1]

4,4,5,5-Tetramethyl-2-(2-methyl-3-furanyl)-1,3,2-dioxaborolane (412 mg, 1.980 mmol) was added to a solution of cis-4-(6-bromo-2-pyridinyl)-2,6-dimethylmorpholine (537 mg, 1.980 mmol) in a mixture of 1,4-dioxane (15 mL), water (2.500 mL) and sodium carbonate (420 mg, 3.96 mmol). The solution was degassed using argon gas and then charged with tetrakis(triphenylphosphine)palladium(0) (229 mg, 0.198 mmol). After addition, the reaction mixture was stirred and heated in the microwave at 100° C. for 1 hour. Crude LC/MS showed starting material and desired product so tetrakis (triphenylphosphine) palladium(0) (229 mg, 0.198 mmol), sodium carbonate (420 mg, 3.96 mmol) and 4,4,5,5-tetramethyl-2-(2-methyl-3-furanyl)-1,3,2-dioxaborolane (412 mg, 1.980 mmol) were added to the reaction mixture which was then stirred and heated at 100° C. in the microwave for 1 hour. Crude LC/MS showed desired product and no starting material can be seen. The reaction mixture was washed with ethyl acetate (200 mL), water (100 mL), filtered and then evaporated to dryness. The residue was dissolved in dichloromethane (~5 ml) and purified on silica by a Biotage SP4 chromatographic system (40+M cartridge, eluted with 0-50% ethyl acetate in isohexanes). Fractions containing pure product were combined and concentrated under reduced pressure to give the title compound as a colourless oil (270 mg, 0.942 mmol, 47.6% yield). LC/MS [M+H]$^+$=273.

Intermediate 22: cis-4-[5-Bromo-6-(2-methyl-3-furanyl)-2-pyridinyl]-2,6-dimethylmorpholine

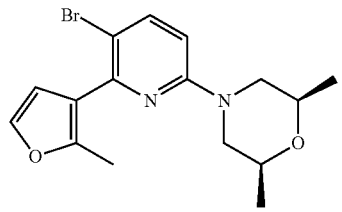 [SMILES: Cc1occc1-c1nc(N2C[C@@H](C)O[C@@H](C)C2)ccc1Br]

N-Bromosuccinimide (137 mg, 0.771 mmol) was added portionwise to a solution of cis-2,6-dimethyl-4-[6-(2-methyl-3-furanyl)-2-pyridinyl]morpholine (210 mg, 0.771 mmol) in chloroform (7 mL) at 0° C. The reaction was stirred at 0° C. for 1 hour. Crude LC/MS showed desired product can be seen and no starting material left, so the reaction mixture was diluted with ethyl acetate (20 mL) and washed with water (10 mL), brine (10 mL), water (10 mL) and brine (10 mL). The organic layer was dried (sodium sulfate), filtered and concentrated under reduced pressure. The residue was dissolved in dichloromethane (~10 ml) and purified on silica by a Biotage SP4 chromatographic system (40+S cartridge, eluted with 0-100% ethyl acetate in isohexanes). Fractions containing pure product were combined and concentrated under reduced pressure to give the title compound as a colourless oil (280 mg, 0.678 mmol, 88% yield). LC/MS [M+H]$^+$=351/353.

Intermediate 23: cis-4-(3-Chlorophenyl)-2,6-dimethylmorpholine

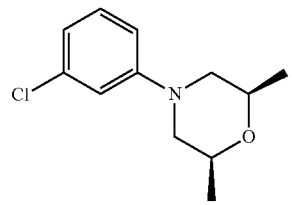

1-Chloro-3-iodobenzene (3.09 g, 12.96 mmol) was dissolved in 1,4-dioxane (50 mL). To this was added cis-2,6-dimethylmorpholine (1.492 g, 12.96 mmol), caesium carbonate (6.33 g, 19.44 mmol) and BINAP (1.210 g, 1.944 mmol) and the solution was degassed by sonication under argon. To this was added palladium(II) acetate (0.145 g, 0.648 mmol) and the solution was refluxed at 130° C. under argon overnight. Crude LC/MS showed desired product and no starting material so the reaction mixture was filtered through celite, eluting with ethyl acetate. The filtrate was diluted with water and the aqueous phase was separated and re-extracted using ethyl acetate (×3). The combined organic layers were washed with brine, separated, dried over magnesium sulphate, filtered and concentrated under pressure. The residue was dissolved in dichloromethane (~10 ml) and purified on silica by using a Biotage SP4 chromatographic system (65i cartridge, eluted with 0-35% ethyl acetate in isohexanes). Fractions containing pure product were combined and concentrated under reduced pressure to give the title compound as a yellow oil (1.785 g, 7.51 mmol, 58.0% yield). LC/MS [M+H]$^+$=226/228.

Intermediate 24: cis-2,6-Dimethyl-4-[3-(2-methyl-3-furanyl)phenyl]morpholine

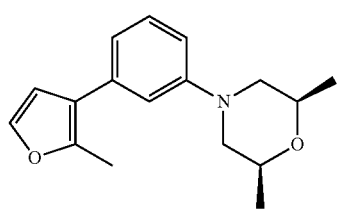 [SMILES: Cc1occc1-c1cccc(N2C[C@@H](C)O[C@@H](C)C2)c1]

4,4,5,5-Tetramethyl-2-(2-methyl-3-furanyl)-1,3,2-dioxaborolane (1.645 g, 7.91 mmol) was added to a solution of cis-4-(3-chlorophenyl)-2,6-dimethylmorpholine (1.785 g, 7.91 mmol) in a mixture of 1,4-dioxane (17 mL), water (2.83 mL) and sodium carbonate (1.676 g, 15.82 mmol). The solution was degassed using argon gas and then charged with tetrakis(triphenylphosphine)palladium(0) (0.914 g, 0.791 mmol). After addition, the reaction mixture was stirred and heated in the microwave at 100° C. for 48 hours. Crude LC/MS showed desired product and only 26% of starting material can be seen. The reaction mixture was washed with ethyl acetate (200 mL), water (100 mL), filtered and then evaporated to dryness. The residue was dissolved in dichloromethane (~10 ml) and purified on silica by using a Biotage SP4 chromatographic system (65i cartridge, eluted with 0-50% ethyl acetate in isohexanes). Fractions containing pure product were combined and concentrated under reduced pressure to give the title compound as a colourless oil (0.74 g, 2.59 mmol, 32.8% yield). LC/MS [M+H]$^+$=272.

Intermediate 25: cis-4-[4-Bromo-3-(2-methyl-3-furanyl)phenyl]-2,6-dimethylmorpholine

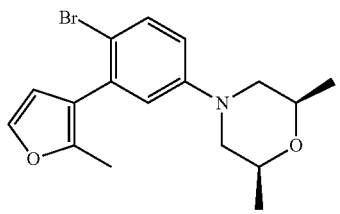 [SMILES: Cc1occc1-c1cc(N2C[C@@H](C)O[C@@H](C)C2)ccc1Br]

N-Bromosuccinimide (380 mg, 2.137 mmol) was added portionwise to a solution of cis-2,6-dimethyl-4-[3-(2-methyl-3-furanyl)phenyl]morpholine (580 mg, 2.137 mmol) in chloroform (10 mL) at 0° C. The reaction was stirred at 0° C. for 1 hour. Crude LC/MS showed desired product can be seen and no starting material left, so the reaction mixture was diluted with ethyl acetate and washed with water, brine, water and brine. The organic layer was dried (sodium sulfate), filtered and concentrated under reduced pressure.

The residue was dissolved in dichloromethane (~10 ml) and purified on silica by using a Biotage SP4 chromatographic system (40+M cartridge, eluted with 0-50% ethyl acetate in isohexanes). Fractions containing pure product were combined and concentrated under reduced pressure to give the title compound as a colourless oil (320 mg, 0.868 mmol, 40.6% yield). LC/MS [M+H]$^+$=350/352.

Intermediate 26: 5-Bromo-2-chloro-4-(methyloxy)pyrimidine

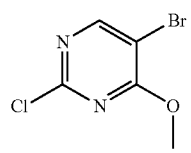

To a solution of 5-bromo-2,4-dichloropyrimidine (17.82 g, 78.2 mmol) in methanol (100 mL) stirred at 0° C. was added solid sodium methoxide (4.22 g, 78 mmol) portionwise during 5 minutes. The reaction mixture was stirred at 23° C. overnight. To the organic phase was added water (25 mL) and the methanol was removed. Then it was extracted with dichloromethane. The organic phase was dried over sodium sulphate and evaporated in vacuo to give the title compound as a white solid (17.2 g, 67.6 mmol, 86 yield). LC/MS [M+H]$^+$=223/225.

Intermediate 27: cis-4-[5-Bromo-4-(methyloxy)-2-pyrimidinyl]-2,6-dimethylmorpholine

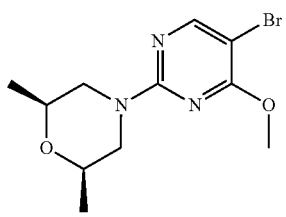

To a solution of 5-bromo-2-chloro-4-methoxypyrimidine (17.2 g, 77 mmol) stirred in air at 0° C. was added neat cis-2,6-dimethylmorpholine (24.5 g, 213 mmol) dropwise in 10 minutes. The reaction mixture was stirred at 45° C. for 30 minutes. The organic phase was evaporated in vacuo to give the crude product as a white solid. The crude product was added to a silica gel column and was eluted with hexane/ethyl acetate (20/1). Collected fractions were evaporated to give the title compound as white solid (17.4 g, 49.3 mmol, 64.1% yield). LC/MS [M+H]$^+$=302/304.

Intermediate 28: cis-2,6-Dimethyl-4-[4-(methyloxy)-5-(2-methyl-4-pyridinyl)-2-pyrimidinyl]morpholine

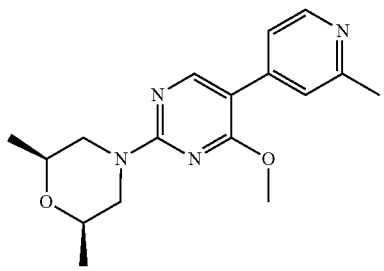

To a suspension of cis-4-(5-bromo-4-methoxypyrimidin-2-yl)-2,6-dimethylmorpholine (671 mg, 2.22 mmol), 2-methyl-4-(4,4,5,5-tetramethyl-1,3,2-dioxaborolan-2-yl)pyridine (632 mg, 2.89 mmol) and potassium carbonate (798 mg, 5.77 mmol) in 1,4-dioxane (3 mL) and water (0.5 mL) stirred in air at 20° C. was added solid tetrakis(triphenylphosphine)palladium(0) (128 mg, 0.111 mmol). The reaction mixture was stirred under argon at 100° C. overnight. The reaction mixture was allowed to cool to room temperature, diluted with water and extracted with ethyl acetate (×3). The ethyl acetate layers were combined, dried over magnesium sulfate and evaporated under reduced pressure. The crude product was added to a silica gel column and was eluted with dichloromethane/methanol/triethylamine (20:1:0.5). Collected fractions were evaporated to give the title compound (120 mg, 0.031 mmol, 1.393% yield). LC/MS [M+H]⁺=318.

Intermediate 29: 2-[cis-2,6-dimethyl-4-morpholinyl]-5-(2-methyl-4-pyridinyl)-4(1H)-pyrimidinone

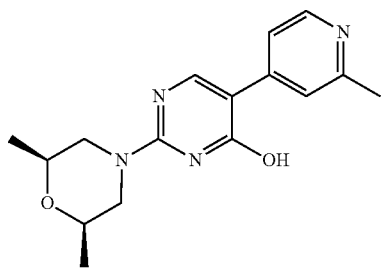

2,6-Dimethyl-4-[4-(methyloxy)-5-(2-methyl-4-pyridinyl)-2-pyrimidinyl]morpholine (1.42 g, 4.52 mmol) was dissolved in 33% hydrobromic acid in acetic acid (45.4 ml, 836 mmol) and heated at 80° C. for 18 hours. It was confirmed reaction had progressed to completion by LC/MS. The reaction mixture was allowed to cool to room temperature. The product was then diluted with methanol and passed down a 50 g SCX column. The impurities were eluted with methanol, followed by elution of the product with 2M ammonia/methanol. The fractions containing product were combined and evaporated under reduced pressure to give the title compound as a white solid (760 mg, 2.53 mmol, 56.0 yield). LC/MS [M+H]⁺=301.

Intermediate 30: cis-4-[4-Chloro-5-(2-methyl-4-pyridinyl)-2-pyrimidinyl]-2,6-dimethylmorpholine

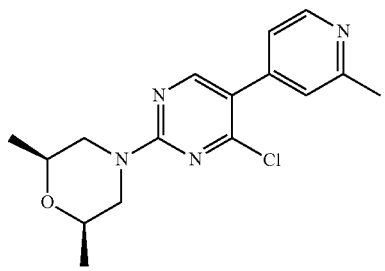

To solid 2-(cis-2,6-dimethylmorpholino)-5-(2-methylpyridin-4-yl)pyrimidin-4-ol (8.3 g, 27.6 mmol) at 20° C. was added neat phosphorus oxychloride (79 ml, 848 mmol). The reaction mixture was stirred at 110° C. for 3 hours. After cooling to 30° C., most of the phosphorus oxychloride was removed and 20 ml of dichloromethane was added. The solution was added into ice-water. The pH was adjusted to 8 using sodium bicarbonate. The dichloromethane layer was separated, washed with water, dried and evaporated. The crude product was added to a silica gel column and was eluted with dichloromethane and then dichloromethane/methanol (5:1).

Collected fractions were evaporated to give the title compound (680 mg, 1.960 mmol, 7.09% yield). LC/MS [M+H]⁺=319/321.

Intermediate 31: 2-Chloro-4-(2-methyl-3-furanyl)pyrimidine

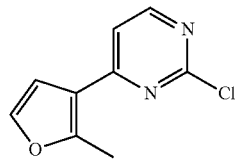

2,4-Dichloropyrimidine (1.0 g, 6.71 mmol), 4,4,5,5-tetramethyl-2-(2-methyl-3-furanyl)-1,3,2-dioxaborolane (1.397 g, 6.71 mmol), sodium carbonate (1.067 g, 10.07 mmol) and tetrakis(triphenylphosphine)palladium(0) (0.388 g, 0.336 mmol) were added together in 1,4-dioxane (42 mL) and water (7.00 mL) and the resulting mixture was heated at 85° C. under argon for 4 hours. The reaction mixture was allowed to cool to room temperature, diluted with water and extracted with ethyl acetate (×3). The ethyl acetate layers were combined, dried over magnesium sulfate and evaporated under reduced pressure. The residue was purified by Biotage SP4 column chromatography eluting with a gradient of 0-30% ethyl acetate and iso-hexane. Product containing fractions were combined and evaporated under reduced pressure to give the title compound (686 mg, 3.52 mmol, 52.5 yield) as a white solid. LC/MS [M+H]⁺=195/197.

Intermediate 32: cis-2,6-dimethyl-4-[4-(2-methyl-3-furanyl)-2-pyrimidinyl]morpholine

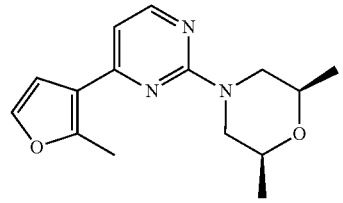 [SMILES: Cc1occc1-c1ccnc(N2C[C@@H](C)O[C@@H](C)C2)n1]

2-Chloro-4-(2-methyl-3-furanyl)pyrimidine (686 mg, 3.52 mmol), cis-2,6-dimethylmorpholine (447 mg, 3.88 mmol) and potassium carbonate (536 mg, 3.88 mmol) were added together in ethanol (16 mL) and the resulting mixture was heated under reflux for 4 hours. A further quantity of cis-2,6-dimethylmorpholine (122 mg, 1.057 mmol) and potassium carbonate (146 mg, 1.057 mmol) were added and the resulting mixture was heated under reflux for 4 hours. The reaction mixture was allowed to cool to room temperature and left to stand overnight. The reaction mixture was filtered, the filtrate evaporated under reduced pressure and the residue purified by SP4 Biotage column chromatography eluting with a gradient of 0-30% ethyl acetate and iso-hexane. Product containing fractions were combined and evaporated under reduced pressure to give the title compound (737 mg, 2.70 mmol, 76% yield) as a colourless oil. LC/MS [M+H]⁺=274.

Intermediate 33: cis-4-[5-Bromo-4-(2-methyl-3-furanyl)-2-pyrimidinyl]-2,6-dimethylmorpholine

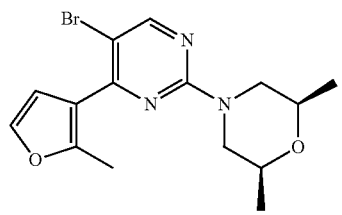

2,6-Dimethyl-4-[4-(2-methyl-3-furanyl)-2-pyrimidinyl]morpholine (737 mg, 2.70 mmol) was dissolved in chloroform (13 mL), cooled in an ice bath and treated with N-bromosuccinimide (480 mg, 2.70 mmol). The resulting mixture was stirred at 0° C. for 1 hour. The reaction mixture was diluted with water and extracted with ethyl acetate (×2). The ethyl acetate layers were combined, dried over magnesium sulfate and evaporated under reduced pressure. The residue was purified by SP4 Biotage column chromatography eluting with a gradient of 0-20% ethyl acetate in iso-hexane. Product containing fractions were combined and evaporated under reduced pressure to give the title compound (719 mg, 2.041 mmol, 76% yield) as a white solid. LC/MS [M+H]⁺=352/354.

Example 1

4-(2-Methyl-3-furanyl)-2-(3-methyl-1-piperidinyl)-5-(4-pyridinyl)pyrimidine hydrochloride

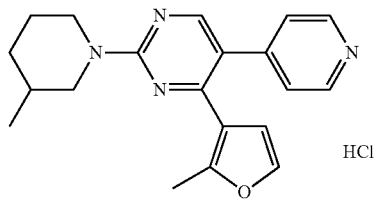 [SMILES: Cc1occc1-c1nc(N2CCCC(C)C2)ncc1-c1ccncc1 ; Cl]

A mixture of 3-(dimethylamino)-1-(2-methyl-3-furanyl)-2-(4-pyridinyl)-2-propen-1-one (256 mg, 1 mmol) and 3-methyl-1-piperidinecarboximidamide hydrochloride (267 mg, 1.500 mmol) in ethanol (5 ml) was stirred at room temperature. Potassium tert-butoxide (224 mg, 2.000 mmol) was added and the mixture was heated at reflux for 45 minutes. After cooling to room temperature the reaction mixture was diluted with water and extracted with ethyl acetate. The organic extracts were combined, washed with water and brine, dried and evaporated. The residue was purified by silica gel chromatography eluting with 25-50% ethyl acetate and isohexane to give 4-(2-methyl-3-furanyl)-2-(3-methyl-1-piperidinyl)-5-(4-pyridinyl)pyrimidine (195 mg, 58%). A solution of 4-(2-methyl-3-furanyl)-2-(3-methyl-1-piperidinyl)-5-(4-pyridinyl)pyrimidine (167 mg, 0.5 mmol) in dichloromethane (1 ml) was treated with hydrogen chloride (1M in diethyl ether, 0.6 ml). The solvent was evaporated and the residue co-evaporated with diethyl ether (×2). The residue was triturated with diethyl ether and the resulting solid was collected, washed with diethyl ether and dried to give the title compound as a yellow solid (121 mg, 65%). LC/MS [M+H]⁺=335. ¹H NMR (400 MHz, d6-DMSO): δ 8.76 (1H, d), 8.57 (1H, s), 7.80 (2H, d), 7.51 (1H, d), 6.00 (1H, d), 4.67-4.60 (2H, m), 3.06-2.99 (1H, m), 2.67-2.76 (1H, m), 2.37 (3H, s), 1.91-1.19 (5H, m), 0.93 (3H, d).

Example 2

4-(2-Methyl-3-furanyl)-2-(3-methyl-1-piperidinyl)-5-(3-pyridinyl)pyrimidine hydrochloride

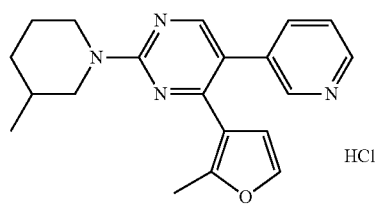 [SMILES: Cc1occc1-c1nc(N2CCCC(C)C2)ncc1-c1cccnc1 ; Cl]

A mixture of 3-(dimethylamino)-1-(2-methyl-3-furanyl)-2-(3-pyridinyl)-2-propen-1-one (256 mg, 1 mmol) and 3-methyl-1-piperidinecarboximidamide hydrochloride (267 mg, 1.5 mmol) in ethanol (5 ml) was stirred at room temperature. Potassium tert-butoxide (224 mg, 2 mmol) was added and the mixture was heated at reflux for 45 minutes. After cooling to room temperature the reaction mixture was diluted with water and extracted with ethyl acetate. The organic extracts were combined, washed with water and brine, dried and evaporated. The residue was purified by silica gel chromatography eluting with 25% ethyl acetate and isohexane to give 4-(2-methyl-3-furanyl)-2-(3-methyl-1-piperidinyl)-5-(3-pyridinyl)pyrimidine (28 mg, 8%). A solution of 4-(2-methyl-3-furanyl)-2-(3-methyl-1-piperidinyl)-5-(3-pyridinyl)pyrimidine (28 mg, 0.084 mmol) in dichloromethane (1 ml) was treated with hydrogen chloride (1M in diethyl ether, 0.1 ml). The solvent was evaporated and the residue co-evaporated with dichloromethane (×2). The resulting solid was dried to give the title compound as a solid (24 mg, 77%). LC/MS [M+H]⁺=335. ¹H NMR (400 MHz, d6-DMSO): δ 8.75-8.73 (2H, m), 8.45 (1H, s), 8.17 (1H, d), 7.86-7.82 (1H, m), 7.45 (1H, d), 5.87 (1H, d), 4.65-4.59 (2H, m), 3.02-2.95 (1H, m), 2.71-2.65 (1H, m), 2.38 (3H, s), 1.91-1.18 (5H, m), 0.92 (3H, d).

Example 3

4-(2-Methyl-3-furanyl)-2-(3-methyl-1-piperidinyl)-5-(2-methyl-4-pyridinyl)pyrimidine hydrochloride

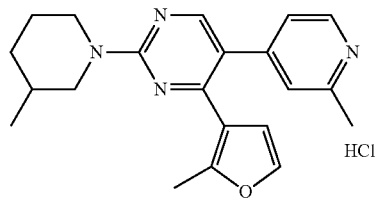 [SMILES: Cc1cc(-c2cnc(N3CCCC(C)C3)nc2-c2ccoc2C)ccn1 ; Cl]

A mixture of 3-(dimethylamino)-1-(2-methyl-3-furanyl)-2-(2-methyl-4-pyridinyl)-2-propen-1-one (541 mg, 2.000 mmol) and 3-methyl-1-piperidinecarboximidamide hydrochloride (533 mg, 3 mmol) in ethanol (10 ml) was stirred at room temperature. Potassium tert-butoxide (449 mg, 4.00 mmol) was added and the mixture was heated at reflux for 90 minutes. After cooling to room temperature the solvent was evaporated and the residue was diluted with water and extracted with ethyl acetate. The organic extracts were combined, washed with water and brine, dried and evaporated. The residue was purified by silica gel chromatography eluting with 25% ethyl acetate in isohexane to give 4-(2-methyl-3-furanyl)-2-(3-methyl-1-piperidinyl)-5-(2-methyl-4-pyridinyl)pyrimidine as a gum (460 mg, 66%). A solution of 4-(2-methyl-3-furanyl)-2-(3-methyl-1-piperidinyl)-5-(2-methyl-4-pyridinyl)pyrimidine (460 mg, 1.3 mmol) in dichloromethane (2 ml) was treated with hydrogen chloride (1M in diethyl ether, 1.5 ml). The solvent was evaporated and the residue was co-evaporated with diethyl ether (×2). The residue was triturated with diethyl ether and the resulting solid was collected, washed with diethyl ether and dried to give the title compound as a pale yellow solid (450 mg, 89%). LC/MS [M+H]$^+$=349. $^1$H NMR (400 MHz, d6-DMSO): δ 8.59 (1H, d), 8.54 (1H, s), 7.81 (1H, s), 7.57-7.52 (1H, m), 7.51 (1H, d), 6.02 (1H, d), 4.70-4.60 (2H, m), 3.06-2.98 (1H, m), 2.70-2.77 (1H, m), 2.66 (3H, s), 2.39 (3H, s), 1.84-1.19 (5H, m), 0.93 (3H, d).

Example 4

4-(2-Methyl-3-furanyl)-5-(2-methyl-4-pyridinyl)-2-(1-piperidinyl)pyrimidine hydrochloride

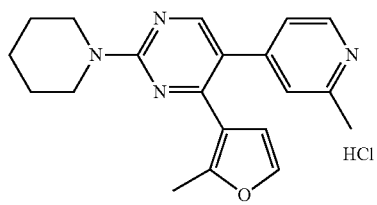 [SMILES: Cc1cc(-c2cnc(N3CCCCC3)nc2-c2ccoc2C)ccn1 ; Cl]

A mixture of 3-(dimethylamino)-1-(2-methyl-3-furanyl)-2-(2-methyl-4-pyridinyl)-2-propen-1-one (270 mg, 1 mmol) and 1-piperidinecarboximidamide hydrochloride (245 mg, 1.500 mmol) in ethanol (4 ml) was stirred at room temperature. Potassium tert-butoxide (224 mg, 2.000 mmol) was added and the mixture was heated at reflux for 90 minutes. After cooling to room temperature the solvent was evaporated and the residue was diluted with water and extracted with ethyl acetate. The organic extracts were combined, washed with water and brine, dried and evaporated. The residue was purified by silica gel chromatography eluting with 30-100% ethyl acetate in isohexane. The resulting oil was dissolved in dichloromethane (2 ml) and was treated with hydrogen chloride (1M in diethyl ether, 1 ml). The solvent was evaporated and the residue co-evaporated with diethyl ether (×2). The residue was triturated with diethyl ether and the resulting solid was collected, washed with diethyl ether and dried to give the title compound as a pale yellow solid (114 mg, 31%). LC/MS [M+H]$^+$=335. $^1$H NMR (400 MHz, d6-DMSO): δ 8.60 (2H, d), 8.55 (1H, s), 7.83 (1H, b), 7.58-7.54 (1H, m), 7.51 (1H, d), 6.03 (1H, d), 3.90-3.85 (4H, m), 2.67 (3H, s), 2.38 (3H, s), 1.70-1.53 (6H, m).

Example 5 cis-2,6-Dimethyl-4-[4-(2-methyl-3-furanyl)-5-(2-methyl-4-pyridinyl)-2-pyrimidinyl]morpholine hydrochloride

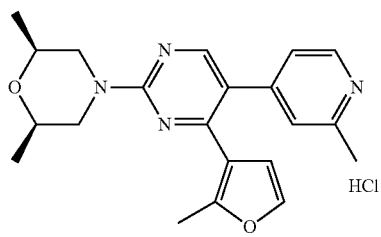 [SMILES: Cc1cc(-c2cnc(N3C[C@@H](C)O[C@@H](C)C3)nc2-c2ccoc2C)ccn1 ; Cl]

A mixture of 3-(dimethylamino)-1-(2-methyl-3-furanyl)-2-(2-methyl-4-pyridinyl)-2-propen-1-one (1352 mg, 5 mmol) and 2,6-dimethyl-4-morpholinecarboximidamide hydrochloride (1453 mg, 7.50 mmol) (ca. 2.3:1 mixture of cis:trans isomers) in ethanol (10 ml) was stirred at room temperature. Potassium tert-butoxide (1122 mg, 10.00 mmol) was added and the mixture was heated at reflux for 3 hours. After cooling to room temperature the solvent was evaporated and the residue was diluted with water and extracted with ethyl acetate. The organic extracts were combined, washed with water and brine, dried and evaporated. The residue was purified by silica gel chromatography eluting with 50% ethyl acetate in isohexane to give cis-2,6-dimethyl-4-[4-(2-methyl-3-furanyl)-5-(2-methyl-4-pyridinyl)-2-pyrimidinyl]morpholine as an oil (200 mg). The cross-over fractions from the column (~800 mg) were purified by mass-directed automated HPLC to give additional cis-2,6-dimethyl-4-[4-(2-methyl-3-furanyl)-5-(2-methyl-4-pyridinyl)-2-pyrimidinyl]morpholine (200 mg) and trans-2,6-dimethyl-4-[4-(2-methyl-3-furanyl)-5-(2-methyl-4-pyridinyl)-2-pyrimidinyl]morpholine (49 mg). A solution of cis-2,6-dimethyl-4-[4-(2-methyl-3-furanyl)-5-(2-methyl-4-pyridinyl)-2-pyrimidinyl]morpholine (200 mg, 0.55 mmol) was dissolved in dichloromethane (2 ml) and hydrogen chloride (1M in ether, 0.6 ml) was added. The solvent was evaporated and the residue was evaporated with ether (×2) and then triturated with ether. The solid was collected, washed with ether and dried to give the title compound (178 mg). LC/MS [M+H]$^+$=365. $^1$H NMR (400 MHz, d6-DMSO): δ 8.61 (1H, d), 8.56 (1H, s), 7.82 (1H, b), 7.58-7.53 (1H, m), 7.52 (1H, d), 6.04 (1H, d), 4.65-4.58 (2H, m), 3.64-3.55 (2H, m), 2.72-2.63 (2H, m), 2.66 (3H, s), 2.36 (3H, s), 1.18 (6H, d).

Example 6 trans-2,6-Dimethyl-4-[4-(2-methyl-3-furanyl)-5-(2-methyl-4-pyridinyl)-2-pyrimidinyl]morpholine hydrochloride

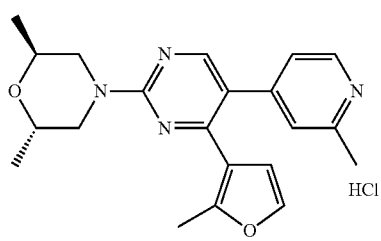 [SMILES: Cc1cc(-c2cnc(N3C[C@H](C)O[C@@H](C)C3)nc2-c2ccoc2C)ccn1 ; Cl]

A solution of trans-2,6-dimethyl-4-[4-(2-methyl-3-furanyl)-5-(2-methyl-4-pyridinyl)-2-pyrimidinyl]morpholine (49 mg, 0.13 mmol), isolated from the crude product obtained in Example 5 by silica gel chromatography and HPLC as described above, was dissolved in dichloromethane (2 ml) and hydrogen chloride (1M in ether, 0.15 ml) was added. The solvent was evaporated and the residue was evaporated with ether (×2) and then triturated with ether. The solid was collected, washed with ether and dried to give the title compound (38 mg). LC/MS [M+H]$^+$=365. $^1$H NMR (400 MHz, d6-DMSO): δ 8.61 (2H, d), 8.55 (1H, s), 7.81 (1H, b), 7.58-7.54 (1H, m), 7.51 (1H, d), 6.02 (1H, d), 4.08-4.01 (2H, m), 3.98-3.91 (1H, m), 3.62-3.52 (2H, m), 1.16 (6H, d).

Example 7

1-[4-(2-Methyl-3-furanyl)-5-(2-Pyridinyl)-2-pyrimidinyl]hexahydro-1H-azepine hydrochloride

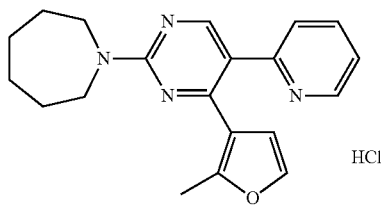 [SMILES: Cc1occc1-c1nc(N2CCCCCC2)ncc1-c1ccccn1 ; Cl]

A mixture of 3-(dimethylamino)-1-(2-methyl-3-furanyl)-2-(2-pyridinyl)-2-propen-1-one (205 mg, 0.8 mmol) and hexahydro-1H-azepine-1-carboximidamide hydrochloride (213 mg, 1.200 mmol) in ethanol (4 ml) was stirred at room temperature. Potassium tert-butoxide (180 mg, 1.600 mmol) was added and the mixture was heated at reflux for 45 minutes. After cooling to room temperature the reaction mixture was diluted with water and extracted with ethyl acetate. The organic extracts were combined, washed with water and brine, dried and evaporated. The residue was purified by mass-directed automated HPLC. The product was dissolved in a mixture of dichloromethane (2 ml) and methanol (0.5 ml) and hydrogen chloride (1M in ether, 0.5 ml) was added and the solvent was evaporated. The residue was co-evaporated with ether and triturated with ether. The solid was collected and dried to give the title compound (67 mg, 23%). LC/MS [M+H]$^+$=335. $^1$H NMR (400 MHz, d6-DMSO): δ 8.74 (2H, d), 8.54 (1H, s), 8.12-8.10 (1H, m), 7.65-7.55 (2H, m), 7.43 (1H, d), 5.74 (1H, d), 3.84-3.80 (4H, m), 2.41 (3H, s), 1.85-1.70 (4H, m), 1.60-1.48 (4H, m).

Example 8

4-(2-Methyl-3-furanyl)-2-(3-methyl-1-piperidinyl)-5-(2-pyridinyl)pyrimidine hydrochloride

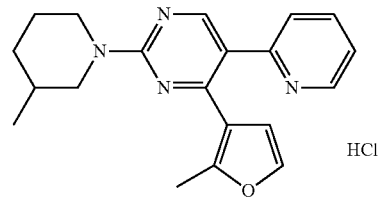 [SMILES: Cc1occc1-c1nc(N2CCCC(C)C2)ncc1-c1ccccn1 ; Cl]

A mixture of 3-(dimethylamino)-1-(2-methyl-3-furanyl)-2-(2-pyridinyl)-2-propen-1-one (256 mg, 1 mmol) and 3-methyl-1-piperidinecarboximidamide hydrochloride (267 mg, 1.5 mmol) in ethanol (5 ml) was stirred at room temperature. Potassium tert-butoxide (224 mg, 2 mmol) was added and the mixture was heated at reflux for 45 minutes. After cooling to room temperature the reaction mixture was diluted with water and extracted with ethyl acetate. The organic extracts were combined, washed with water and brine, dried and evaporated. The residue was purified by silica gel chromatography eluting with 25% ethyl acetate and isohexane followed by mass-directed automated HPLC to give 4-(2-methyl-3-furanyl)-2-(3-methyl-1-piperidinyl)-5-(2-pyridinyl)pyrimidine (223 mg, 67%).

A solution of 4-(2-methyl-3-furanyl)-2-(3-methyl-1-piperidinyl)-5-(2-pyridinyl)pyrimidine (200 mg, 0.6 mmol) in dichloromethane (2 ml) was treated with hydrogen chloride (1M in diethyl ether, 0.8 ml). The solvent was evaporated and the residue co-evaporated with dichloromethane (×2). The resulting solid was dried to give the title compound as a pale yellow solid (160 mg, 43%). LC/MS [M+H]$^+$=335. $^1$H NMR (400 MHz, d6-DMSO): δ 8.77 (1H, d), 8.56 (1H, s), 8.25-8.21 (1H, m), 7.74-7.65 (2H, m), 7.45 (1H, d), 7.78 (1H, d), 4.66-4.60 (2H, m), 3.12-2.98 (1H, m), 2.75-2.66 (1H, m), 2.40 (3H, s), 1.90-1.20 (5H, m), 0.93 (3H, d).

Example 9 cis-2,6-Dimethyl-4-[4-(2-methylpropyl)-5-(2-methyl-4-pyridinyl)-2-pyrimidinyl]morpholine hydrochloride

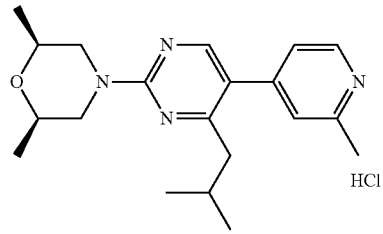 [SMILES: Cc1cc(-c2cnc(N3C[C@@H](C)O[C@@H](C)C3)nc2CC(C)C)ccn1 ; Cl]

A mixture of cis-4-[4-chloro-5-(2-methyl-4-pyridinyl)-2-pyrimidinyl]-2,6-dimethylmorpholine (100 mg, 0.314 mmol) and copper (I) iodide (11.95 mg, 0.063 mmol) in tetrahydrofuran (1 ml) was stirred at 0° C. under argon and isobutyl magnesium chloride (2M solution in tetrahydrofuran) (0.314 ml, 0.627 mmol) was added dropwise. The reaction mixture was stirred at 0° C. for 90 minutes. Saturated ammonium chloride solution was added and the mixture was extracted with ethyl acetate. The organic extract was separated, washed with saturated ammonium chloride solution, water and brine, dried and evaporated. The residue was purified by silica gel chromatography eluting with 50-100% ethyl acetate in isohexanes. The product (61 mg, 0.18 mmol) was dissolved in dichloromethane (1 ml) and methanol (0.5 ml) and hydrogen chloride (1M in ether, 0.2 ml) was added. The solvent was evaporated and the residue was co-evaporated with ether. The residue was triturated with ether and the resulting solid was collected and dried to give the title compound (48 mg, 41%). LC/MS [M+H]$^+$=341. $^1$H NMR (400 MHz, d6-DMSO): δ 8.74 (1H, d), 8.36 (1H, s), 7.87-7.85 (1H, m), 7.81-7.78 (1H, m), 4.62-4.58 (2H, m), 3.61-3.54 (2H, m), 2.72 (3H, s), 2.63-2.58 (4H, m), 2.15-2.08 (1H, m), 1.18 (6H, d), 0.79 (6H, d).

Example 10 cis-2,6-Dimethyl-4-[6-(2-methyl-3-furanyl)-5-(2-methyl-4-pyridinyl)-2-pyrazinyl]morpholine hydrochloride

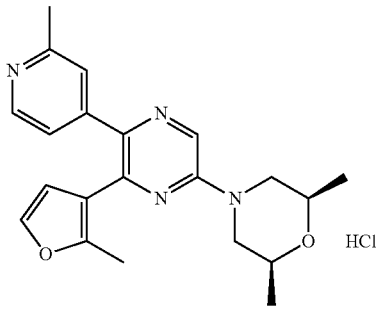 [SMILES: Cc1cc(-c2ncc(N3C[C@@H](C)O[C@@H](C)C3)nc2-c2ccoc2C)ccn1 ; Cl]

2-Methyl-4-(4,4,5,5-tetramethyl-1,3,2-dioxaborolan-2-yl)pyridine (131 mg, 0.596 mmol) was added to a solution of cis-4-[5-bromo-6-(2-methyl-3-furanyl)-2-pyrazinyl]-2,6-dimethylmorpholine (210 mg, 0.596 mmol) in a mixture of 1,4-dioxane (4 mL), water (0.667 mL) and sodium carbonate (126 mg, 1.192 mmol). The solution was degassed using argon gas and then charged with tetrakis(triphenylphosphine) palladium(0) (68.9 mg, 0.060 mmol). After addition, the reaction mixture was stirred and heated in the microwave at 100° C. for 1 hour. LC/MS showed starting material and desired product so the reaction mixture was stirred and heated at 100° C. in the microwave for a further 1 hour. Crude LC/MS showed desired product and no starting material can be seen. The reaction mixture was washed with ethyl acetate (200 mL), water (100 mL), filtered and then evaporated to dryness. The resulting solid was dissolved in 1:1 MeCN:DMSO (2.7 mL) and purified by MDAP. Fractions containing pure product were combined and concentrated under reduced pressure. 1.1 equivalents of HCl in diethyl ether were added to form the HCl salt and the resulting mixture was evaporated under reduced pressure to give the title compound as a yellow solid (37 mg, 0.088 mmol, 14.71% yield).

LC/MS [M+H]$^+$=365; $^1$H NMR (400 MHz, d$_4$-MeOD): δ 8.50-8.48 (1H, d), 8.37 (1H, s), 8.02 (1H, s), 7.89-7.87 (1H, d), 7.43-7.42 (1H, d), 6.26-6.25 (1H, d), 4.45-4.42 (2H, d), 3.77-3.69 (2H, m), 2.78-2.73 (5H, m), 2.29 (3H, s), 1.27-1.25 (6H, d).

Example 11

6-(cis-2,6-dimethyl-4-morpholinyl)-2'-methyl-4-(2-methyl-3-furanyl)-3,4'-bipyridine hydrochloride

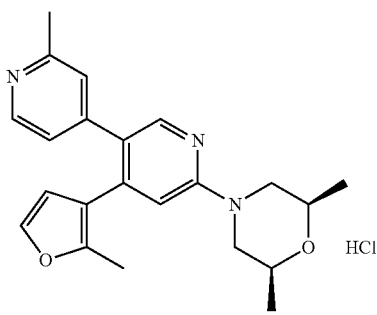 [SMILES: Cc1cc(-c2cnc(N3C[C@@H](C)O[C@@H](C)C3)cc2-c2ccoc2C)ccn1 ; Cl]

2-Methyl-4-(4,4,5,5-tetramethyl-1,3,2-dioxaborolan-2-yl)pyridine (184 mg, 0.840 mmol) was added to a solution of cis-4-[5-bromo-4-(2-methyl-3-furanyl)-2-pyridinyl]-2,6-dimethylmorpholine (295 mg, 0.840 mmol) in a mixture of 1,4-dioxane (6 mL), water (1.000 mL) and sodium carbonate (178 mg, 1.680 mmol). The solution was degassed using argon gas and then charged with tetrakis(triphenylphosphine) palladium(0) (97 mg, 0.084 mmol). After addition, the reaction mixture was stirred and heated in the microwave at 100° C. for 1 hour. Crude LCMS showed starting material and desired product so the reaction mixture was stirred and heated at 100° C. in the microwave for a further 1 hour. Crude LCMS showed desired product and no starting material can be seen. The reaction mixture was washed with ethyl acetate (200 mL), water (100 mL), filtered and then evaporated to dryness. This solid was dissolved in 1:1 MeCN:DMSO (5×0.9 mL) and purified by MDAP. Fractions containing pure product were combined and concentrated under reduced pressure. 1.1 equivalents of HCl in diethyl ether were added to form the HCl salt and the resulting mixture was evaporated under reduced pressure to give the title compound as a yellow solid (141 mg, 0.335 mmol, 39.9% yield).

LC/MS [M+H]$^+$=364; $^1$H NMR (400 MHz, d$_4$-MeOD): δ 8.56-8.55 (1H, d), 8.30 (1H, s), 7.87 (1H, s), 7.64-7.63 (1H, m), 7.45-7.43 (1H, d), 7.25 (1H, s), 6.19-6.20 (1H, d), 4.25-4.22 (2H, d), 3.82-3.75 (2H, m), 2.92-2.86 (2H, m), 2.76 (3H, s), 2.19 (3H, s), 1.29-1.27 (6H, d).

Example 12

6-(cis-2,6-dimethyl-4-morpholinyl)-2'-methyl-2-(2-methyl-3-furanyl)-3,4'-bipyridine hydrochloride

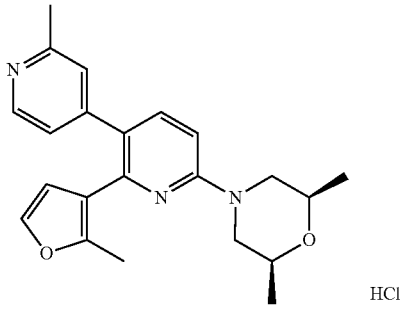 [SMILES: Cc1cc(-c2ccc(N3C[C@@H](C)O[C@@H](C)C3)nc2-c2ccoc2C)ccn1 ; Cl]

2-Methyl-4-(4,4,5,5-tetramethyl-1,3,2-dioxaborolan-2-yl)pyridine (175 mg, 0.797 mmol) was added to a solution of cis-4-[5-bromo-6-(2-methyl-3-furanyl)-2-pyridinyl]-2,6-dimethylmorpholine (280 mg, 0.797 mmol) in a mixture of 1,4-dioxane (4 mL), water (0.667 mL) and sodium carbonate (169 mg, 1.594 mmol). The solution was degassed using argon gas and then charged with tetrakis(triphenylphosphine) palladium(0) (92 mg, 0.080 mmol). After addition, the reaction mixture was stirred and heated in the microwave at 100° C. for 1 hour. Crude LC/MS showed starting material and desired product so the reaction mixture was stirred and heated at 100° C. in the microwave for a further 1 hour. Crude LC/MS showed desired product and no starting material can be seen. The reaction mixture was washed with ethyl acetate (200 mL), water (100 mL), filtered and then evaporated to dryness. This solid was dissolved in 1:1 MeCN:DMSO (3.6 mL) and purified by MDAP. Fractions containing pure product were combined and concentrated under reduced pressure. This solid was dissolved in 1:1 MeCN:DMSO (1.8 mL) and purified again by MDAP. Fractions containing pure product were combined and concentrated under reduced pressure. 1.1 equivalents of HCl in diethyl ether was added to form the HCl salt and the resulting mixture was evaporated under reduced pressure to give the title compound as a yellow oil (25 mg, 0.059 mmol, 7.45% yield). LC/MS [M+H]$^+$=364; $^1$H NMR (400 MHz, d$_4$-MeOD): δ 8.61-8.60 (1H, d), 8.26-8.24 (1H, d), 7.93 (1H, s), 7.69-7.67 (1H, d), 7.63-7.60 (1H, d), 7.56 (1H, s), 6.59 (1H, s), 4.22-4.19 (2H, d), 3.86-3.79 (2H, m), 3.06-3.00 (2H, m), 2.78 (3H, s), 2.10 (3H, s), 1.29-1.27 (6H, d).

Example 13 cis-2,6-Dimethyl-4-[3-(2-methyl-3-furanyl)-4-(2-methyl-4-pyridinyl)phenyl]morpholine

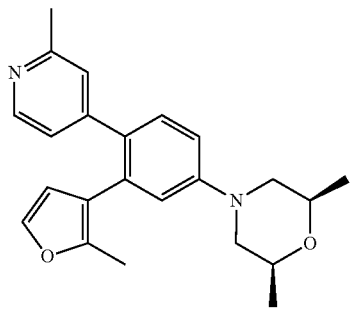 [SMILES: Cc1cc(-c2ccc(N3C[C@@H](C)O[C@@H](C)C3)cc2-c2ccoc2C)ccn1]

2-Methyl-4-(4,4,5,5-tetramethyl-1,3,2-dioxaborolan-2-yl)pyridine (313 mg, 1.428 mmol) was added to a solution of cis-4-[4-bromo-3-(2-methyl-3-furanyl)phenyl]-2,6-dimethylmorpholine (500 mg, 1.428 mmol) in a mixture of 1,4-dioxane (6 mL), water (1.000 mL) and sodium carbonate (303 mg, 2.86 mmol). The solution was degassed using argon gas and then charged with tetrakis(triphenylphosphine)palladium(0) (165 mg, 0.143 mmol). After addition, the reaction mixture was stirred and heated in the microwave at 100° C. overnight. Crude LCMS showed starting material and desired product so 2-methyl-4-(4,4,5,5-tetramethyl-1,3,2-dioxaborolan-2-yl)pyridine (0.5 equivalents), tetrakis(triphenylphosphine)palladium(0) (0.05 equivalents) and sodium carbonate (1.0 equivalent) were added and the reaction mixture was stirred and heated at 100° C. in the microwave for a further 1 hour. Crude LCMS showed desired product and no starting material can be seen. The reaction mixture was washed with ethyl acetate (200 mL), water (100 mL), filtered and then evaporated to dryness. The residue was dissolved in dichloromethane (~10 ml) and purified on silica by using a Biotage SP4 chromatographic system (40+M cartridge, eluted with 0-50% ethyl acetate in isohexanes). Fractions containing pure product were combined and concentrated under reduced pressure. This solid was dissolved in 1:1 MeCN:DMSO (3×0.9 mL) and purified by MDAP. Fractions containing pure product were combined and concentrated under reduced pressure to give the title compound as a yellow oil (169 mg, 0.443 mmol, 31.0% yield).

LC/MS [M+H]$^+$=363; $^1$H NMR (400 MHz, d$_4$-MeOD): δ 8.50-8.48 (1H, d), 7.79 (1H, s), 7.70-7.68 (1H, d), 7.61-7.59 (1H, d), 7.48-7.45 (1H, m), 7.39-7.40 (1H, d), 7.34 (1H, s), 6.25-6.24 (1H, d), 4.03-3.96 (2H, m), 3.76-3.73 (2H, d), 2.88-2.82 (2H, m), 2.74 (3H, s), 2.02 (3H, s), 1.28-1.26 (6H, d).

Example 14 cis-2,6-Dimethyl-4-[4-(2-methylphenyl)-5-(2-methyl-4-pyridinyl)-2-pyrimidinyl]morpholine

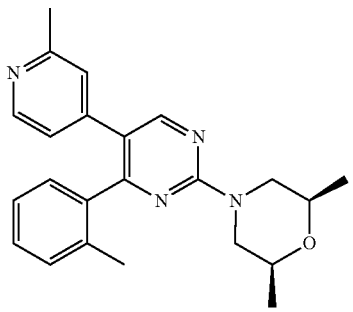 [SMILES: Cc1cc(-c2cnc(N3C[C@@H](C)O[C@@H](C)C3)nc2-c2ccccc2C)ccn1]

To a suspension of cis-4-(4-chloro-5-(2-methylpyridin-4-yl)pyrimidin-2-yl)-2,6-dimethylmorpholine (0.100 g, 0.314 mmol), o-tolylboronic acid (0.064 g, 0.471 mmol) and potassium carbonate (0.138 g, 1 mmol) in 1,4-dioxane (3 mL) and water (0.5 mL) stirred in air at 20° C. was added solid tetrakis (triphenylphosphine)palladium(0) (0.058 g, 0.0500 mmol). The reaction mixture was stirred under nitrogen at 100° C. overnight. The reaction mixture was allowed to cool to room temperature, diluted with water and extracted with ethyl acetate (×3). The ethyl acetate layers were combined, dried under magnesium sulfate and evaporated under reduced pressure. The crude product was purified by pre-HPLC, (Gilson GX-281; Shimadzu 15 um 250*19 mm; A:10 mMol NH$_4$HCO$_3$/Water B: CH$_3$CN; 0-7 min 85-95%, 7-14 min 95%; 214 nm; 30 mL/min) to obtain the title compound (35.4 mg, 0.095 mmol, 30.1% yield). LC/MS [M+H]$^+$=375; $^1$H NMR (400 MHz, CDCl$_3$): δ 8.41 (1H, s), 8.27-8.25 (1H, s), 7.29-7.25 (1H, m), 7.17-7.14 (2H, m), 7.10-7.09 (1H, m), 6.81 (1H, s), 6.69-6.67 (1H, d), 4.69-4.65 (2H, d), 3.72-3.63 (2H, m), 2.69-2.63 (2H, m), 2.43 (3H, s), 2.07 (3H, s), 1.27-1.26 (6H, d).

Example 15 cis-2,6-dimethyl-4-[4-(2-methyl-3-furanyl)-5-(3-methyl-4-pyridinyl)-2-pyrimidinyl]morpholine hydrochloride

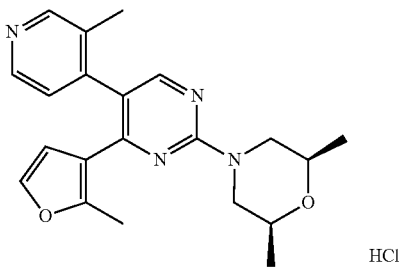 [SMILES: Cc1cnccc1-c1cnc(N2C[C@@H](C)O[C@@H](C)C2)nc1-c1ccoc1C ; Cl]

cis-4-[5-Bromo-4-(2-methyl-3-furanyl)-2-pyrimidinyl]-2,6-dimethylmorpholine (100 mg, 0.284 mmol), 3-methyl-4- pyridinyl)boronic acid HCl (54.2 mg, 0.312 mmol), sodium carbonate (75 mg, 0.710 mmol) and tetrakis(triphenylphosphine)palladium(0) (16.40 mg, 0.014 mmol) were added together in 1,4-dioxane (3 mL) and water (0.500 mL) and the resulting mixture was heated at 85° C. under argon for 4 hours. A further amount of (3-methyl-4-pyridinyl)boronic acid HCl (54.2 mg, 0.312 mmol), sodium carbonate (75 mg, 0.710 mmol) and tetrakis (16.40 mg, 0.014 mmol) were added and the resulting mixture was heated at 85° C. under argon for 18 hours. The reaction mixture was allowed to cool to room temperature, diluted with water and extracted with ethyl acetate (×3). The ethyl acetate layers were combined, dried over magnesium sulfate and evaporated under reduced pressure. The residue was purified by Biotage SP4 column chromatography eluting with a gradient of 0-60% ethyl acetate and iso-hexane. Product containing fractions were combined and evaporated under reduced pressure. The residue was dissolved in methanol (1 ml), treated with 1M HCl in ether (0.1 mL, 0.100 mmol) and evaporated under reduced pressure. The resulting solid was dried under high vacuum at 40° C. for 18 hours to give the title compound (34 mg, 0.085 mmol, 29.9% yield) as a white solid. LC/MS [M+H]$^+$=365; $^1$H NMR (400 MHz, d$_4$-MeOD): δ 8.68-8.66 (2H, m), 8.33 (1H, s), 7.92-7.90 (1H, d), 7.25-7.24 (1H, d), 5.75-5.74 (1H, d), 4.74-4.70 (2H, m), 3.72-3.64 (2H, m), 2.73-2.67 (2H, m), 2.49 (3H, s), 2.18 (3H, s), 1.25-1.24 (6H, m).

Example 16 cis-2,6-Dimethyl-4-{5-(2-methyl-4-pyridinyl)-4-[2-(trifluoromethyl)-3-pyridinyl]-2-pyrimidinyl}morpholine hydrochloride

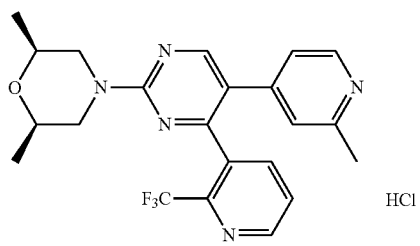 [SMILES: Cc1cc(-c2cnc(N3C[C@@H](C)O[C@@H](C)C3)nc2-c2cccnc2C(F)(F)F)ccn1 ; Cl]

Sodium carbonate (166 mg, 1.568 mmol) in water (2 ml), bis(triphenylphosphine) palladium(II)chloride (11.01 mg, 0.016 mmol) and [2-(trifluoromethyl)-3-pyridinyl]boronic acid (90 mg, 0.471 mmol) were added to a solution of cis-4-[4-chloro-5-(2-methyl-4-pyridinyl)-2-pyrimidinyl]-2,6-dimethylmorpholine (100 mg, 0.314 mmol) in 1,2-dimethoxyethane (DME) (3 ml). The reaction mixture was heated to 80° C. for 1 hour. After cooling to room temperature the reaction mixture was partitioned between ethyl acetate (20 mls) and water (20 mls). The organic layer was passed through a hydrophobic frit to remove traces of water and then evaporated to dryness to give a yellow gum. The residue was subject to MDAP purification in 1 ml of 50:50 DMSO:MeOH. Clean fractions were combined and evaporated to dryness to give a yellow gum. The free base was generated by partitioning between sodium bicarbonate and dichloromethane. The organic layer was dried by passing through a hydrophobic frit and then the HCl salt was generated by addition of 1M HCl in diethylether (97 ul). The solvent was evaporated and the residue was co-evaporated with ether. The residue was triturated with ether and the resulting solid was collected and dried at 40° C. under vacuum for 1 hour to give the title compound as a yellow solid (30 mg, 19.5%). LC/MS [M+H]$^+$=430. $^1$H NMR (400 MHz, d6-DMSO): δ 8.64 (1H, s), 8.60 (1H, d), 8.53 (1H, d), 8.32 (1H, t), 7.97 (1H, d), 7.67 (1H, m), 7.53-7.44 (1H, m), 4.70 (2H, d), 3.68-3.55 (2H, m), 2.75-2.65 (2H, m), 2.58 (3H, s), 1.19 (6H, d).

Example 17 cis-4-[4-(6-Fluoro-4-methyl-3-pyridinyl)-5-(2-methyl-4-pyridinyl)-2-pyrimidinyl]-2,6-dimethylmorpholine hydrochloride

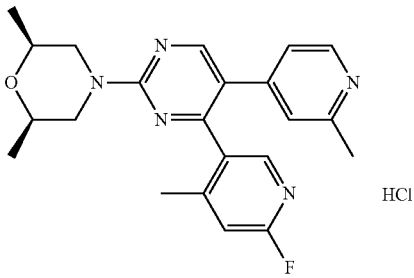 [SMILES: Cc1cc(-c2cnc(N3C[C@@H](C)O[C@@H](C)C3)nc2-c2cnc(F)cc2C)ccn1 ; Cl]

Sodium carbonate (166 mg, 1.568 mmol) in water (2 ml), bis(triphenylphosphine)palladium(II)chloride (11.01 mg, 0.016 mmol) and (6-fluoro-4-methyl-3-pyridinyl)boronic acid (72.9 mg, 0.471 mmol) were added to a solution of cis-4-[4-chloro-5-(2-methyl-4-pyridinyl)-2-pyrimidinyl]-2,6-dimethylmorpholine (100 mg, 0.314 mmol) in 1,2-dimethoxyethane (DME) (3 ml). The reaction mixture was heated to 80° C. for 1 hour. After cooling to room temperature the reaction mixture was partitioned between ethyl acetate (20 mL) and water (20 mL). The organic layer was passed through a hydrophobic frit to remove traces of water and then evaporated to dryness to give a brown gum. The residue was subject to MDAP purification in 1 mL of 50:50 DMSO:MeOH. Clean fractions were combined and evaporated to dryness to give a white solid. The free base was generated by partitioning between sodium bicarbonate and dichloromethane. The organic layer was dried by passing through a hydrophobic frit and then the HCl salt was generated by addition of 1M HCl in diethylether (132 ul). The solvent was evaporated and the residue was co-evaporated with ether. The residue was triturated with ether and the resulting solid was collected and dried at 40° C. under vacuum for 1 hour to give the title compound as a cream solid (9 mg, 6%). LC/MS [M+H]$^+$=394. $^1$H NMR (400 MHz, d6-DMSO): δ 8.74 (1H, s), 8.49 (1H, d), 7.96 (1H, s), 7.65 (1H, s), 7.20 (1H, d), 7.17 (1H, s), 4.67-4.50 (2H, m), 3.70-3.44 (2H, m, hidden under water peak), 2.73-2.63 (2H, m), 2.59 (3H, s), 2.20 (3H, s), 1.17 (6H, d).

Example 18 cis-2-[2-(2,6-Dimethyl-4-morpholinyl)-5-(2-methyl-4-pyridinyl)-4-pyrimidinyl]-4-fluorobenzonitrile hydrochloride

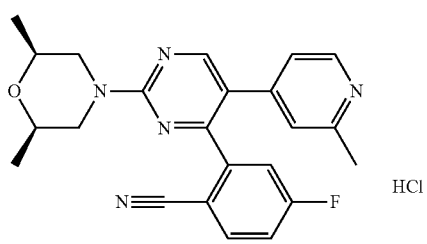 [SMILES: Cc1cc(-c2cnc(N3C[C@@H](C)O[C@@H](C)C3)nc2-c2cc(F)ccc2C#N)ccn1 ; Cl]

Sodium carbonate (166 mg, 1.568 mmol) in water (2 mL), bis(triphenylphosphine) palladium(II) chloride (11.01 mg, 0.016 mmol) and 2-cyano-5-fluorophenylboronic acid pinacol ester (155 mg, 0.627 mmol) were added to a solution of cis-4-[4-chloro-5-(2-methyl-4-pyridinyl)-2-pyrimidinyl]-2,6-dimethylmorpholine (100 mg, 0.314 mmol) in 1,2-dimethoxyethane (3 mL). The reaction mixture was heated to 100° C. for 2 hour. The reaction mixture diluted with water (5 mL) and extracted with DCM (5 mL×2). The organic extracts were combined, dried (MgSO$_4$), filtered and the solvent was removed. The resulting residues were then purified by MDAP and fractions containing desired product were combined and evaporated to give a solid. The solid was then dissolved in methanol (2 mL) and 4M HCl in dioxane (1 mL) was added. The solvent was removed to give the title compound (50 mg). LC/MS [M+H]$^+$=404. $^1$H NMR (400 MHz, d6-DMSO): δ 8.82 (1H, s), 8.56 (1H, d), 8.10-8.05 (1H, m), 7.77-7.79 (1H, m), 7.56-7.62 (1H, m), 7.45-7.39 (2H, m), 4.70-4.66 (1H, m), 3.63-3.57 (2H, m), 2.76-2.68 (2H, m), 2.64 (3H, s), 1.18 (6H, d).

Example 19 cis-2-[2-(2,6-dimethyl-4-morpholinyl)-5-(2-methyl-4-pyridinyl)-4-pyrimidinyl]-6-(trifluoromethyl)benzonitrile hydrochloride

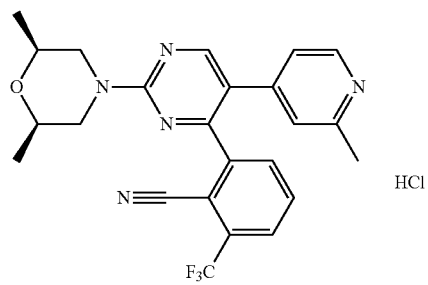 [SMILES: Cc1cc(-c2cnc(N3C[C@@H](C)O[C@@H](C)C3)nc2-c2cccc(C(F)(F)F)c2C#N)ccn1 ; Cl]

Sodium carbonate (166 mg, 1.568 mmol) in water (2 mL), bis(triphenylphosphine) palladium(II) chloride (11.01 mg, 0.016 mmol) and 2-(5,5-dimethyl-1,3,2-dioxaborinan-2-yl)-6-(trifluoromethyl)benzonitrile (178 mg, 0.627 mmol) were added to a solution of cis-4-[4-chloro-5-(2-methyl-4-pyridinyl)-2-pyrimidinyl]-2,6-dimethylmorpholine (100 mg, 0.314 mmol) in 1,2-dimethoxyethane (3 mL). The reaction mixture was heated to 100° C. for 2 hours. The reaction mixture diluted with water (5 mL) and extracted with DCM (5 mL×2). The organic extracts were combined, dried (MgSO$_4$), filtered and the solvent was removed. The resulting residues were then purified by MDAP and fractions containing desired product were combined and evaporated to dryness. The solid was dissolved in methanol (2 mL) and 4M HCl in dioxane (1 mL) was added. The solvent was removed to give the title compound (75 mg). LC/MS [M+H]$^+$=454.

Biological Assay

The PAM activity of the compounds of the invention at the α7 nAChR may be determined using the following cell-based calcium flux assay which uses a Fluorimetric Image Plate Reader (FLIPR) (see Schroeder et al.; *J. Biomolecular Screening*, 1(2), p 75-80, 1996).

GH4C1 cell line stably transfected with human α7 nAChR was suspended in a 384 well plate and incubated at 30° C. for 48 h in a 5% carbon dioxide atmosphere. The growth media was removed and the cells washed three times with a solution of Hanks' balanced salt solution (HBSS), 20 mM HEPES and 2.5 mM probenecid leaving 20 μl washing solution in each well. A loading solution (200) containing HBSS, probenecid, 1-4 μM Fluo4 AM (a calcium indicator dye) and pluronic acid was added and the plate incubated for 45 min at 37° C. under an atmosphere free from carbon dioxide. The cells were washed three times leaving 30 μl in each well. The plate containing the cells and calcium indicator dye were then transferred to the FLIPR. The assay was initiated by collecting baseline datapoints at 10 second intervals followed by addition of the test compound in buffer solution (0.33% DMSO) and diluted to a final concentration of 10 μM and serial dilution of the wells, 1:2 or 1:3, gave a low concentration of <1 nM. Following a further 5-10 mins 10 μl of 50 μM nicotine was added and data collected for 2 to 3 mins. Nicotine produced a rapid, transient and reproducible calcium flux which could be potentiated with the positive allosteric modulator test compounds.

The compounds of Examples 1 to 19 described above and/or salts thereof, for example HCl salts, were screened using the assay described above and gave a pEC$_{50}$ of equal to or greater than 5.0 (ie an EC$_{50}$ of 10$^{-5}$ M or less) with a maximum potentiation of the response area to approximately 1200% relative to nicotine control as shown in table 1 below:

TABLE 1

| Example | MOLSTRUCTURE | a7 new sm > PXC50 MEAN |
|---------|--------------|------------------------|
| 1       |              | ***                    |
| 2       |              | *                      |
| 3       |              | ***                    |

TABLE 1-continued

| Example | MOLSTRUCTURE | a7 new sm > PXC50 MEAN |
|---------|--------------|------------------------|
| 4 | | *** |
| 5 | | *** |
| 6 | | *** |
| 7 | | * |
| 8 | | ** |
| 9 | | *** |
| 10 | | ** |
| 11 | | ** |
| 12 | | ** |

TABLE 1-continued

| Example | MOLSTRUCTURE | a7 new sm > PXC50 MEAN |
|---------|--------------|------------------------|
| 13 | | *** |
| 14 | | ** |
| 15 | | ** |
| 16 | | * |
| 17 | | ** |
| 18 | | * |
| 19 | | *** |

In addition, the following compounds commercially available from Asinex of Moscow, Russia or Specs of Delft, the Netherlands were screened using the assay described above and gave a $pEC_{50}$ of equal to or greater than 5.0 with a maximum potentiation of the response area to approximately 1200% relative to nicotine control as shown in table 2 below:

TABLE 2
| MOLSTRUCTURE | a7 new sm > PXC50 MEAN | SUPPLIER | SUPPLIER_ID |
|---|---|---|---|
| 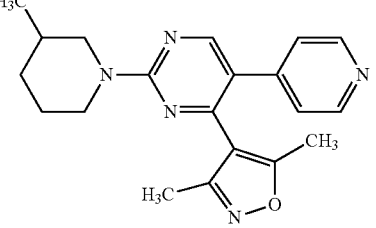 | ** | ASINEX | AOP 14465526 |
| 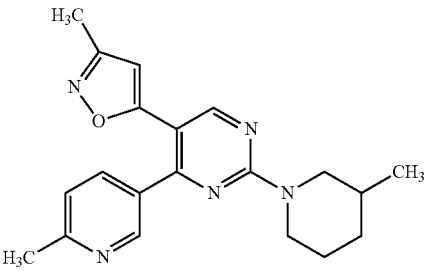 | *** | ASINEX | ADM 14220368 |
| 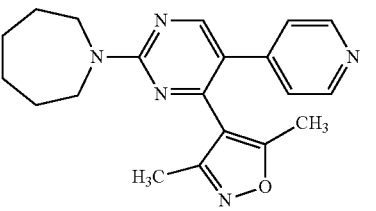 [SMILES: Cc1noc(C)c1-c1nc(N2CCCCCC2)ncc1-c1ccncc1] | ** | ASINEX | AOP 14465544 |
| 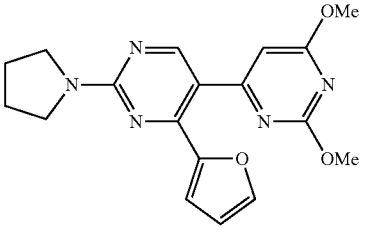 [SMILES: COc1cc(-c2cnc(N3CCCC3)nc2-c2ccco2)nc(OC)n1] | * | ASINEX | ATL 14631887 |
| 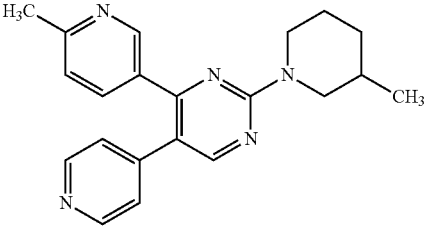 | *** | ASINEX | AOP 13274016 |
| 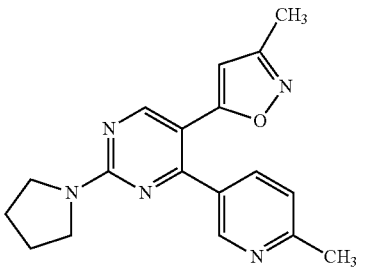 [SMILES: Cc1ccc(-c2nc(N3CCCC3)ncc2-c2cc(C)no2)cn1] | * | ASINEX | ADM 14220366 |

TABLE 2-continued

| MOLSTRUCTURE | a7 new sm > PXC50 MEAN | SUPPLIER | SUPPLIER_ID |
| --- | --- | --- | --- |
| | * | ASINEX | ATL 14631888 |
| | *** | ASINEX | ADM 14220371 |
| | *** | ASINEX | ADM 14465558 |
| | ** | ASINEX | ADM 14408364 |
| | *** | SPECS | AO-476/43380313 |
| | ** | ASINEX | LMK 13280444 |

TABLE 2-continued

| MOLSTRUCTURE | a7 new sm > PXC50 MEAN | SUPPLIER | SUPPLIER_ID |
| --- | --- | --- | --- |
| (structure) | * | ASINEX | AOP 14465529 |
| (structure) | ** | ASINEX | ATL 13269690 or ADM 13269690 |
| (structure) | ** | ASINEX | AEM 14465590 |
| (structure) | *** | ASINEX | ADM 13269676 |
| (structure) | * | ASINEX | LMK 13268083 |
| (structure) | ** | ASINEX | ADM 13269686 |

TABLE 2-continued

| MOLSTRUCTURE | a7 new sm > PXC50 MEAN | SUPPLIER | SUPPLIER_ID |
|---|---|---|---|
| 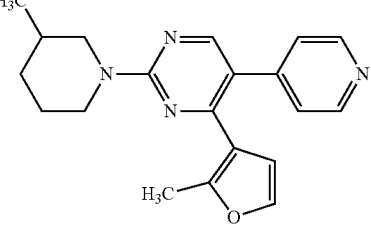 | *** | ASINEX | ADM 13269678 |
| 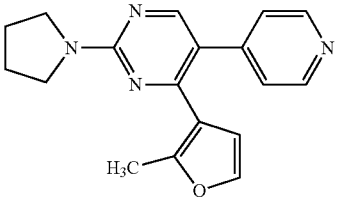 [SMILES: Cc1occc1-c1nc(N2CCCC2)ncc1-c1ccncc1] | ** | ASINEX | ADM 13269675 |
| 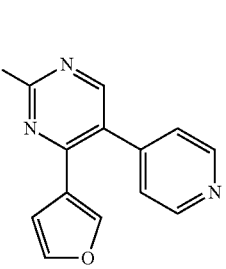 | * | ASINEX | ADM 14465561 |
| 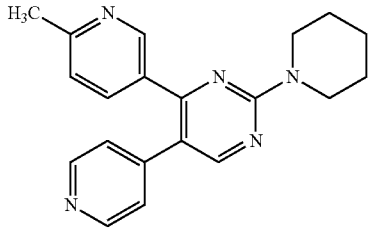 [SMILES: Cc1ccc(-c2nc(N3CCCCC3)ncc2-c2ccncc2)cn1] | ** | ASINEX | AOP 13274014 |
| 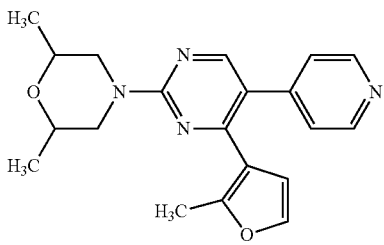 [SMILES: Cc1occc1-c1nc(N2CC(C)OC(C)C2)ncc1-c1ccncc1] | *** | ASINEX | ADM 13269721 |
| 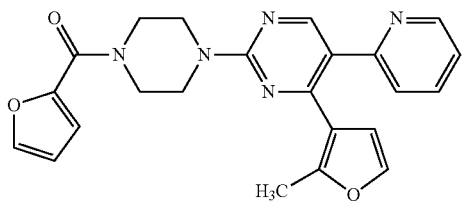 [SMILES: Cc1occc1-c1nc(N2CCN(C(=O)c3ccco3)CC2)ncc1-c1ccccn1] | * | ASINEX | ADM 13270126 |

A value of * in table 1 or table 2 above indicates $pEC_{50}$ of equal to or greater than 5.0, a value of  indicates a $pEC_{50}$ of equal to or greater than 5.5 and a value of * indicates a $pEC_{50}$ of equal to or greater than 6.0 with a maximum potentiation of the response area to approximately 1200% relative to nicotine control.

The following compounds/salts were screened using the assay described above and gave a pEC$_{50}$ of less than 5.0 with a maximum potentiation of the response area to approximately 1200% relative to nicotine control:

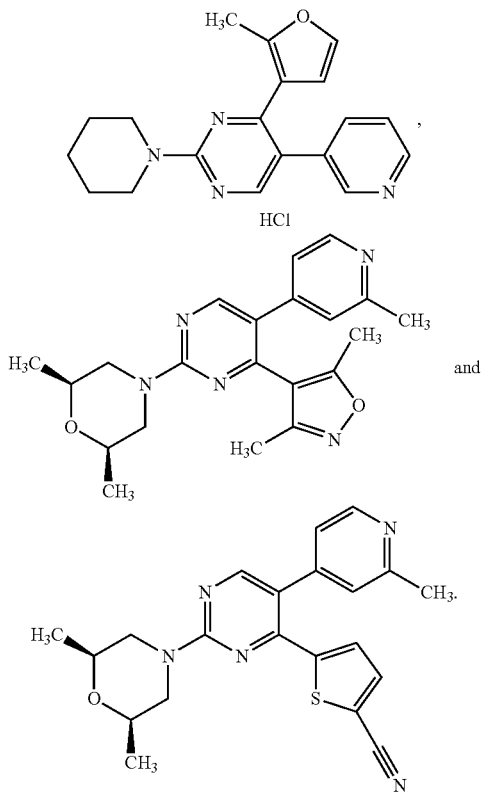

The following compound was screened using the assay described above and gave a pEC$_{50}$ of approximately 5.6 with a maximum potentiation of the response area to approximately 1200% relative to nicotine control. However, when a further batch of the following compound (as the HCl salt) was screened using the assay described above and gave a pEC$_{50}$ of less than 5.0 with a maximum potentiation of the response area to approximately 1200% relative to nicotine control:

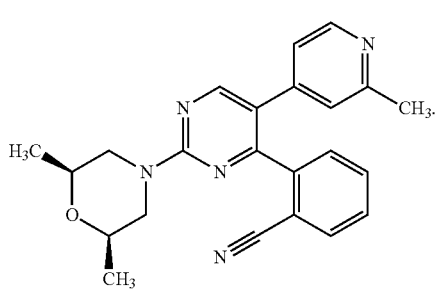

In vivo assays with utility for the evaluation of activity of nicotinic α7 receptor positive modulators include, but are not limited to: cognition assays in both naïve and pharmacologically-impaired animals including delayed matching and non-matching to position, passive avoidance, novel object recognition, Morris water maze (or variants thereof), radial arm maze, five choice serial reaction time task, and cued/contextual fear conditioning; sensory gating assays in both naïve and pharmacologically-impaired animals including pre-pulse inhibition of the startle reflex and auditory gating; and assays of drug—(e.g. amphetamine, morphine, phencyclidine) induced locomotor activity.

The invention claimed is:

1. A compound of the formula (1a), or a pharmaceutically acceptable salt thereof:

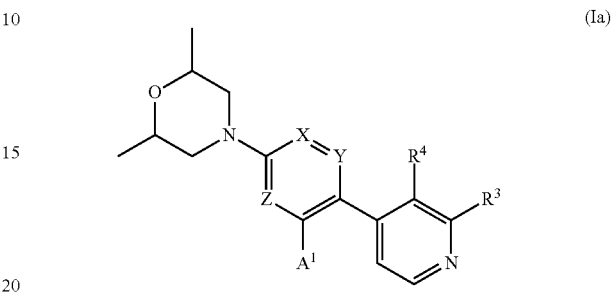

(Ia)

wherein:
X, Y and Z are each independently selected from CH and N;
A$^1$ is selected from an isobutyl and a 5 or 6-membered aryl or heteroaryl, wherein said 5 or 6-membered aryl or heteroaryl is selected from a carbon-linked phenyl, pyridinyl, pyrimidinyl, furyl, pyrrolyl, thienyl or isoxazolyl, each optionally substituted with one or two substituents independently selected from halo, cyano, methyl, trifluoromethyl, methoxy and trifluoromethoxy; and
one of R$^3$ and R$^4$ is hydrogen and the other is methyl.

2. A compound according to claim 1 wherein Y is CH.

3. The compound according to claim 1, or a pharmaceutically acceptable salt thereof, wherein A$^1$ is selected from isobutyl, phenyl, carbon-linked pyridinyl or carbon-linked furyl, said phenyl, pyridinyl or furyl each optionally substituted with one or two substituents independently selected from halo, cyano, methyl, trifluoromethyl, methoxy and trifluoromethoxy.

4. The compound according to claim 1, or a pharmaceutically acceptable salt thereof, wherein the compound is other than:

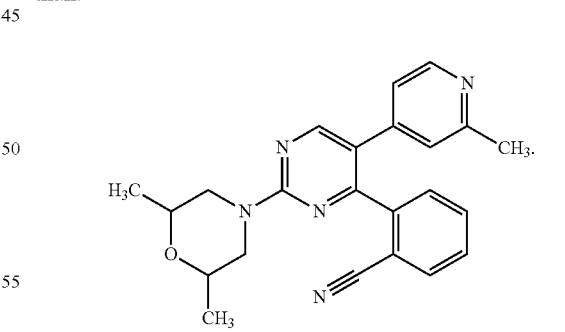

5. The compound according to claim 1, which is:
cis-4-[4-(6-Fluoro-4-methyl-3-pyridinyl)-5-(2-methyl-4-pyridinyl)-2-pyrimidinyl]-2,6-dimethylmorpholine, or a pharmaceutically acceptable salt thereof.

6. A compound which is:
cis-2,6-Dimethyl-4-[4-(2-methyl-3-furanyl)-5-(2-methyl-4-pyridinyl)-2-pyrimidinyl]morpholine;
trans-2,6-Dimethyl-4-[4-(2-methyl-3-furanyl)-5-(2-methyl-4-pyridinyl)-2-pyrimidinyl]morpholine;

cis-2,6-Dimethyl-4-[4-(2-methylpropyl)-5-(2-methyl-4-pyridinyl)-2-pyrimidinyl]morpholine;
cis-2,6-Dimethyl-4-[6-(2-methyl-3-furanyl)-5-(2-methyl-4-pyridinyl)-2-pyrazinyl]morpholine;
6-(cis-2,6-dimethyl-4-morpholinyl)-2'-methyl-4-(2-methyl-3-furanyl)-3,4'-bipyridine;
6-(cis-2,6-dimethyl-4-morpholinyl)-2'-methyl-2-(2-methyl-3-furanyl)-3,4'-bipyridine;
cis-2,6-Dimethyl-4-[3-(2-methyl-3-furanyl)-4-(2-methyl-4-pyridinyl)phenyl]morpholine;
cis-2,6-Dimethyl-4-[4-(2-methylphenyl)-5-(2-methyl-4-pyridinyl)-2-pyrimidinyl]morpholine;
cis-2,6-dimethyl-4-[4-(2-methyl-3-furanyl)-5-(3-methyl-4-pyridinyl)-2-pyrimidinyl]morpholine;
cis-2,6-Dimethyl-4-[5-(2-methyl-4-pyridinyl)-4-[2-(trifluoromethyl)-3-pyridinyl]-2-pyrimidinyl]morpholine;
cis-4-[4-(6-Fluoro-4-methyl-3-pyridinyl)-5-(2-methyl-4-pyridinyl)-2-pyrimidinyl]-2,6-dimethylmorpholine;
cis-2-[2-(2,6-Dimethyl-4-morpholinyl)-5-(2-methyl-4-pyridinyl)-4-pyrimidinyl]-4-fluorobenzonitrile;
cis-2-[2-(2,6-dimethyl-4-morpholinyl)-5-(2-methyl-4-pyridinyl)-4-pyrimidinyl]-6-(trifluoromethyl)benzonitrile;
or a pharmaceutically acceptable salt thereof.

7. A method of treating pain, a psychotic disorder, cognitive impairment or Alzheimer's disease in a human having the pain, a psychotic disorder, cognitive impairment or Alzheimer's disease, the method comprising administering an effective amount of a compound of claim 1, or a pharmaceutically acceptable salt thereof.

8. A method of treating schizophrenia in a human having schizophrenia, the method comprising administering an effective amount of a compound of claim 1, or a pharmaceutically acceptable salt thereof.

9. A method of treating neuropathic pain in a human having neuropathic pain, the method comprising administering an effective amount of a compound of claim 1, or a pharmaceutically acceptable salt thereof.

10. A pharmaceutical composition comprising:
   a compound as defined in claim 1 or a pharmaceutically acceptable salt thereof; and
   one or more pharmaceutically acceptable carriers or excipients.

11. The pharmaceutical composition of claim 10, further comprising: a therapeutic agent.

\* \* \* \* \*